US010228307B2

(12) United States Patent
Javed

(10) Patent No.: US 10,228,307 B2
(45) Date of Patent: Mar. 12, 2019

(54) DISSOLVABLE SAMPLE COLLECTION MATRICES AND METHODS OF USING THE SAME

(71) Applicant: BIOFUNCTIONS, INC., Hawthorne, NY (US)

(72) Inventor: Ali A. Javed, Chappaqua, NY (US)

(73) Assignee: Biofunctions, Inc., Hawthorne, NY (US)

(*) Notice: Subject to any disclaimer, the term of this patent is extended or adjusted under 35 U.S.C. 154(b) by 0 days.

(21) Appl. No.: 15/265,607

(22) Filed: Sep. 14, 2016

(65) Prior Publication Data

US 2018/0045615 A1  Feb. 15, 2018

Related U.S. Application Data

(60) Provisional application No. 62/234,206, filed on Sep. 29, 2015.

(51) Int. Cl.
*G01N 1/10* (2006.01)
*C12N 15/10* (2006.01)
(Continued)

(52) U.S. Cl.
CPC ............ *G01N 1/10* (2013.01); *C12N 15/1003* (2013.01); *C12N 15/1006* (2013.01);
(Continued)

(58) Field of Classification Search
None
See application file for complete search history.

(56) References Cited

U.S. PATENT DOCUMENTS 2,156,927 A    5/1939 Sturken
2,185,110 A *  12/1939 Coleman .............. C09D 189/00
                                            106/156.1
(Continued)

FOREIGN PATENT DOCUMENTS

CA    2104079     2/1994
CN    1727471     3/2013
(Continued)

OTHER PUBLICATIONS

Selling et al. (2007) "Effect of Solvent and Temperature on Secondary and Tertiary Structure of Zein by Circular Dichroism" Cereal Chemistry 84(3):265-270.*
(Continued)

*Primary Examiner* — Karen S. Weiler
(74) *Attorney, Agent, or Firm* — Baker & Hostetler LLP

(57) ABSTRACT

Disclosed herein are matrices for isolating a biological macromolecule from a biological sample, the matrix comprising: a biopolymer capable of binding to the biological macromolecule, wherein the biopolymer is about 0% to about 10% dissolvable in water at a pH of about 6 to about 8 and at ambient temperature but is about 10% to 100% dissolvable in a chaotropic solvent or an organic solvent, and wherein the biopolymer is not squid ring teeth protein; and a surfactant, excipient, or combination thereof. Also provided are methods of using, and kits comprising, the matrices. The disclosed matrices aid in collecting and releasing near quantitative amounts of a biological macromolecule from a biological and/or test sample.

21 Claims, 19 Drawing Sheets

(51) Int. Cl.
  *C12Q 1/6806* (2018.01)
  *G01N 1/28* (2006.01)
  *G01N 1/34* (2006.01)
  *B01L 3/00* (2006.01)
  *G01N 1/02* (2006.01)

(52) U.S. Cl.
  CPC ......... *C12Q 1/6806* (2013.01); *G01N 1/2813* (2013.01); *G01N 1/34* (2013.01); *B01L 3/5023* (2013.01); *B01L 3/5029* (2013.01); *C12Q 2527/125* (2013.01); *G01N 2001/028* (2013.01)

(56) References Cited

U.S. PATENT DOCUMENTS

| | | | |
|---|---|---|---|
| 2,250,040 | A | 7/1941 | Sturken |
| 2,377,290 | A | 5/1945 | Coleman |
| 2,563,791 | A | 8/1951 | Lowe |
| 2,622,988 | A | 12/1952 | Leekley |
| 2,791,509 | A | 5/1957 | Cosler |
| 2,959,492 | A | 11/1960 | Baxter |
| 6,020,008 | A * | 2/2000 | Li .................... A23G 4/08 426/3 |
| 6,645,535 | B2 | 11/2003 | Zyck |
| 8,523,937 | B2 | 9/2013 | Lindsay |
| 8,759,075 | B2 | 6/2014 | Morhet et al. |
| 2005/0256001 | A1 | 11/2005 | Smith |
| 2008/0025936 | A1 | 1/2008 | Keller |
| 2014/0303518 | A1 | 10/2014 | Pierce et al. |

FOREIGN PATENT DOCUMENTS

| | | |
|---|---|---|
| EP | 0638803 | 2/1995 |
| WO | WO 2006/088907 | 8/2006 |
| WO | WO 2008/016517 | 2/2008 |
| WO | WO 2010/132453 | 11/2010 |
| WO | WO 2010/132508 | 11/2010 |
| WO | WO 2015/108598 | 7/2015 |

OTHER PUBLICATIONS

Anderson et al., "Zein Extraction from Corn, Corn Products, and Coproducts and Modifications for Various Applications: A Review", Cereal Chem. 88(2): 159-173, 2011.
Verdon et al., "Swabs as DNA Collection Devices for Sampling Different Biological Materials from Different Substrates", Journal of Forensic Sciences, vol. 59, No. 4, Jul. 2014.
Pena-Francesch et al., "Materials Fabrication from Native and Recombinant Thermoplastic Squid Proteins", Advanced Functional Materials, 24, 7401-7509, 2014.
Verdon et al., "Evaluation of Tapelifting as a Collection Method for Touch DNA", Forensic Science International: Genetics, 8, pp. 179-186, 2014.
NFSTC Swab Collection Study, National Institute of Justice, Start date Jun. 1, 2011 End Date Mar. 30, 2012.
Butts et al., Evaluation of DNA Extraction Efficiency, Proceedings of the American Academy of Forensic Sciences, Feb. 2013.
Marshall et al. "Evaluation of a Novel Material, Diomics X-Swab, for collection of DNA", Forensic Science International: Genetics, 12, pp. 192-198, 2014.
Brownlow et al., "A Comparison of DNA Collection and Tetrieval from Two Swab types (Cotton and Nylon Flocked Swab) when Processed Using Three Qiagen Extraction Methods" Journal of Forensic Sciences, vol. 57, No. 3, May 2012.

* cited by examiner

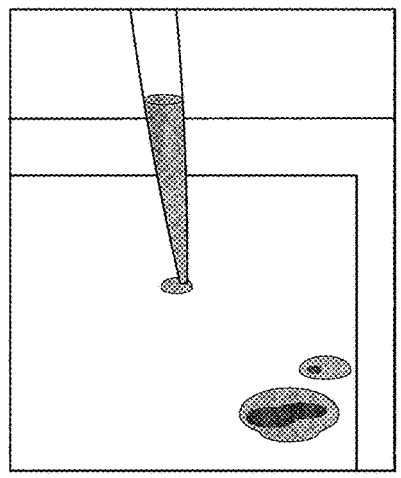
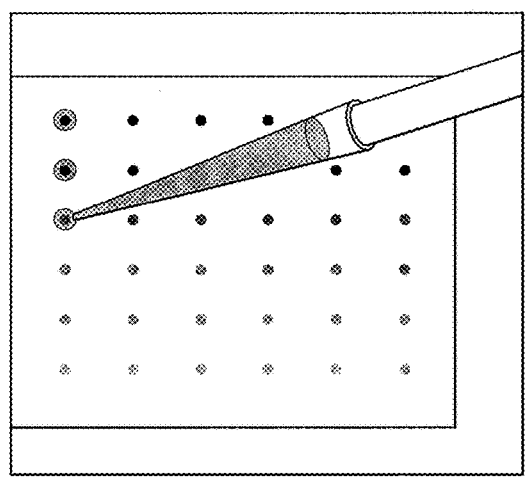
FIG. 2C
FIG. 2D
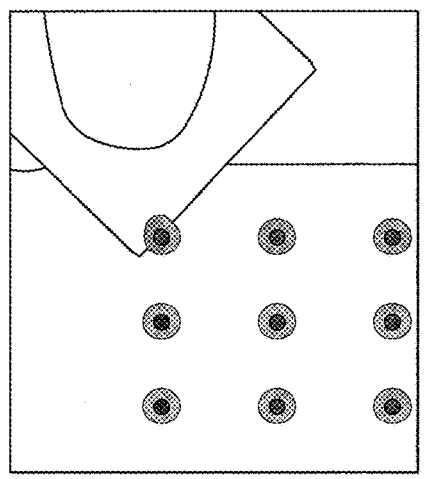
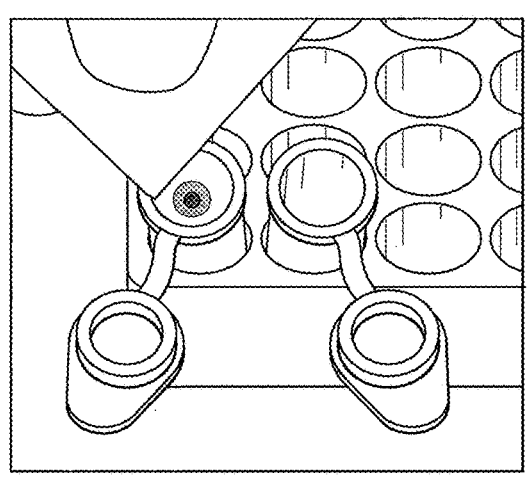
FIG. 2E
FIG. 2F

DISSOLVABLE SAMPLE COLLECTION MATRICES AND METHODS OF USING THE SAME

CROSS REFERENCE TO RELATED APPLICATIONS

This application claims priority to U.S. Provisional Application No. 62/234,206, filed Sep. 29, 2015, the disclosure of which is hereby incorporated by reference in its entirety.

TECHNICAL FIELD

The present disclosure relates to biological sample collection matrices for collecting, extracting, purifying, and testing various biological macromolecules including, but not limited to, DNA, RNA, proteins, drugs, and metabolites.

BACKGROUND

Current sample collection devices for biological materials, including those destined for forensic analysis and DNA biometrics, are ineffective at detecting trace quantities of biological macromolecules (i.e., nanogram to ~100 picograms for nucleic acids or drugs and metabolites) required for sensitive and reliable genetic profiling technology or small molecule detection. The typical sample collection device's matrix is manufactured with cotton, cellulose paper, glass fiber, and more recently, with rayon, nylon, foam, inorganic polysilane, or modified polycaprolactone. As a matrix, cotton—due to its high absorbency—performs optimally in the collection of biological macromolecules but fails to release the collected biological macromolecules quantitatively. Similarly, other matrices perform to varying degrees in the collection of biological macromolecules, but typically lose about 20-80% of the collected biological macromolecules in the release and retrieval steps. A problem with existing matrices for sample collection devices lies in the trapping and irreversibly binding of biological macromolecules to the collection device's matrix.

SUMMARY

Disclosed herein are matrices for isolating a biological macromolecule from a biological sample, the matrices comprising: a biopolymer capable of binding to the biological macromolecule, wherein the biopolymer is about 0% to about 10% dissolvable in water at a pH of about 6 to about 8 and at ambient temperature but is about 10% to 100% dissolvable in a chaotropic solvent or an organic solvent, and wherein the biopolymer is not squid ring teeth protein; and a surfactant, excipient, or combination thereof.

Also provided are devices for isolating a biological macromolecule from a biological sample, the device comprising: a matrix comprising a biopolymer capable of binding to the biological macromolecule, wherein the biopolymer is about 0% to about 10% dissolvable in water at a pH of about 6 to about 8 and at ambient temperature but is about 10% to 100% dissolvable in a chaotropic solvent or an organic solvent, and wherein the biopolymer is not squid ring teeth protein and a surfactant, excipient, or combination thereof; and an applicator, wherein the applicator serves as a substrate for the matrix.

Methods of isolating a biological macromolecule from a biological sample are also provided. The methods comprise contacting the biological sample with any of the herein disclosed matrices or devices; incubating the matrix or device in a chaotropic solvent or an organic solvent; and isolating the biological macromolecule.

Also disclosed are methods of analyzing a test sample for the presence of a biological macromolecule, comprising contacting the test sample with any of the herein disclosed matrices or devices; incubating the matrix or device in a chaotropic solvent or an organic solvent; and analyzing the solvent for the presence of the biological macromolecule.

Also disclosed are devices for collecting, storing, transporting, and/or processing a biological sample, the devices comprising a tube and a spatula, wherein the tube and the spatula are reversibly connected.

BRIEF DESCRIPTION OF THE DRAWINGS

The summary, as well as the following detailed description, is further understood when read in conjunction with the appended drawings. For the purpose of illustrating the disclosed matrices, methods, devices, and kits, there are shown in the drawings exemplary embodiments of the matrices, methods, devices, and kits; however, the matrices, methods, devices, and kits are not limited to the specific embodiments disclosed. In the drawings:

FIG. 2C shows exemplary biopolymer matrix in liquid form applied to blood sample to be collected for DNA extraction.

FIG. 2D shows exemplary biopolymer matrix applied to blood dilutions on a plastic plate to create a dried exemplary biopolymer matrix film.

FIG. 2E shows collection of dried exemplary biopolymer matrix film.

FIG. 2F shows dried exemplary biopolymer matrix film transferred to a tube for DNA extraction.

DETAILED DESCRIPTION OF ILLUSTRATIVE EMBODIMENTS

Figure 1A:
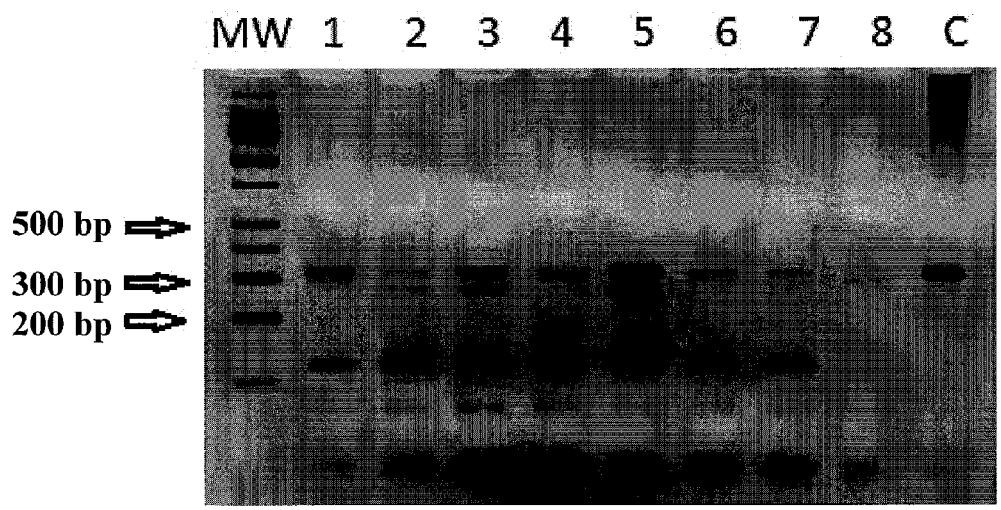
FIG. 1A and FIG. 1B shows a gel electrophoretic representation of the isolation of extracted DNA according to some embodiments.

The disclosed matrices, methods, devices, and kits may be understood more readily by reference to the following detailed description taken in connection with the accompanying figures, which form a part of this disclosure. It is to be understood that the disclosed matrices, methods, devices, and kits are not limited to the specific matrices, methods, devices, and kits described and/or shown herein, and that the terminology used herein is for the purpose of describing particular embodiments by way of example only and is not intended to be limiting of the claimed matrices, methods, devices, and kits.

As used herein, the term "about" is used to encompass variations of ±10% or less, variations of ±5% or less, variations of ±1% or less, variations of ±0.5% or less, or variations of ±0.1% or less from the specified value.

As used herein, "biological pH" encompasses a pH range of about pH 6 to about pH 8.

As used herein, "composite matrix" refers to mixtures of biopolymers with one or more other components, including, for example, proteins, polysaccharides, and/or excipients and other additives.

The term "comprising" is intended to include examples encompassed by the terms "consisting essentially of" and "consisting of"; similarly, the term "consisting essentially of" is intended to include examples encompassed by the term "consisting of."

As used herein, "dissolvable" means that the biopolymer can be fully or partially dissolved, disintegrated, or disrupted in a suitable solvent, thereby releasing/separating the matrix from a biological macromolecule that was bound thereto. "Partially" encompasses greater than about 50% dissolved, disintegrated, or disruption As used herein, "not dissolvable" means that the biopolymer exhibits a solubility of about 0% to about 10% in water at a pH of about 6 to about 8 and at ambient temperature.

As used herein, "touch DNA sample" refers to a sample having epithelial cells that were left behind/deposited due to a person contacting an item surface (such as doorknobs, countertops, cell phone, etc). The touch DNA samples can contain 15-50 shed epithelial cells. Quantitative collection of these samples and retrieval of DNA from these samples can be used for forensic analysis among other things.

As used herein, "reverse touch DNA sample" refers to sample having epithelial cells that were left behind/deposited when the person contacted a preformed sample collection matrix. This type of sample collection can be a structured method of sample collection wherein the subject was touched by, or touched, a preformed matrix film thus depositing epithelial cells on the film upon contact.

Dissolvable Sample Collection Matrices

Disclosed herein are matrices for isolating a biological macromolecule from a biological sample, the matrix comprising: a biopolymer capable of binding to the biological macromolecule, wherein the biopolymer is about 0% to about 10% dissolvable in water at a pH of about 6 to about 8 and at ambient temperature but is about 10% to 100% dissolvable in a chaotropic solvent or an organic solvent, and wherein the biopolymer is not squid ring teeth protein; and a surfactant, excipient, or combination thereof.

Biopolymers include, but are not limited to proteins, polysaccharides, or a combination thereof that are about 10% to about 100% dissolvable in a chaotropic solvent or an organic solvent including, but not limited to, phenol, G-HCl, guanidine thiocyanate, other chaotropic salts, isopropanol, methanol, butanol, formamide, and various combinations of chaotropic salts and buffers. In some embodiments, the biopolymer can be about 10% to about 100% dissolvable in an aqueous solution having a pH below or above biological pH. For example, the solvent can be an aqueous solution having a pH below 3 or a pH above 11.

Biopolymers can be derived from any biological source including animals, plants, and microorganisms. The biopolymers can be naturally occurring proteins, synthetic proteins, or non-naturally occurring proteins.

As a class, most structural proteins (collagen, actin, keratin, etc.), plant storage proteins (prolamins), legume and cupin family of proteins, and casein (milk protein) have about 0% to about 10% dissolvability in water. Any of these proteins are suitable biopolymers for the disclosed matrices. In some embodiments, the biopolymer can comprise collagen, gelatin, prolamin, legume, cupin, or a combination thereof. Thus, in some embodiments, the matrix can comprise collagen, gelatin, prolamin, legume, cupin, or a combination thereof, wherein the collagen, gelatin, prolamin, legume, cupin, or a combination thereof is about 0% to about 10% dissolvable in water at a pH of about 6 to about 8 and at ambient temperature. Suitable prolamins include, but are not limited to, prolamins of wheat (gliadin), barley (horedein), rye (secalin), oat (avenin), or corn (zein) origin. The matrix can comprise a combination of collagen, gelatin, prolamin, legume, or cupin.

Prolamins are a group of plant storage proteins found in the seeds of cereal grains: wheat (gliadin), barley (hordein), rye (secalin), corn (zein), sorghum (kafirin) and as a minor protein, avenin, in oats. They are characterized by a high glutamine and proline content and are generally soluble only in strong alcohol solutions and insoluble in water.

Structural polysaccharides, such as cellulose, and storage polysaccharides (starch and glycogen) are generally about 0% to about 10% dissolvable in water at a pH of about 6 to about 8 and at ambient temperature. Any structural polysaccharide, storage polysaccharide, or other polysaccharide that is about 0% to about 10% dissolvable in water at a pH of about 6 to about 8 and at ambient temperature are suitable biopolymers for the disclosed matrices. In some embodiments, the polysaccharides include, but are not limited to, agarose, starch, cross-linked dextran, or a combination thereof. The biopolymer can be a combination of protein and polysaccharide including, for example, any combination of the above disclosed proteins and polysaccharides.

Suitable surfactants and excipients include glycerol, Sodium Dodecyl Sulfate (SDS), sodium stearate, glyceryl laurate (1-Monolaurin), Polysorbate 20 (polyoxyethylene (20) sorbitan monolaurate; Tween 20), sodium cholate, sodium deoxycholate, DDPS (DPS) N-Dodecyl-N,N-dimethyl-3-ammonio-1-propanesulfonate, 3-(N,N-dimethyl myristyl ammonio) propanesulfonate (TPS), polyoxyethylene (20) cetyl ether (Brij® C10), ethanol, PEG 7000-9000, polyvinyl alcohol, monolaurin. In some embodiments, the biopolymer comprises zein and the surfactant comprises ethanol. In a preferred aspect, the biopolymer comprises about 1% to about 50% zein.

The matrices can further comprise a carbohydrate, salt, organic compound, inorganic compound, or a combination thereof. In some embodiments, the carbohydrate can be starch. Suitable salts include, for example, sodium chloride, ammonium sulfate, ammonium chloride, or a combination thereof. Suitable organic compounds include, for example, sodium stearate, glycerol, glycerol monolaurate, or a combination thereof. Suitable inorganic compounds include, for example, silica.

The matrices can be configured as a composite matrix, layered matrix, extruded fiber, adhesive film, adhesive pad, adhesive spray, foam, liquid, or powder.

The percentage of biopolymer present in the matrix will depend upon the type of surfactant and/or excipient present in the matrix and the configuration of the matrix (i.e. solid, spray, or liquid). Biopolymers in solid form can be configured as a powder, a fiber, or a film, for example. When configured as a solid, the matrix can comprise about 50% to about 100% of biopolymer. Thus, when configured as a solid, the matrix can comprise about 50%, about 60%, about 70%, about 80%, about 90%, or about 100% biopolymer. When configured as a spray, the matrix can comprise about 1% to about 20% of biopolymer. Thus, when configured as a spray, the matrix can comprise about 1%, about 2%, about 4%, about 6%, about 8%, about 10%, about 12%, about 14%, about 16%, about 18%, or about 20% biopolymer. When configured as a liquid, the matrix can comprise about 1% to about 50% of biopolymer. Thus, when configured as a liquid, the matrix can comprise about 1%, about 5%, about 10%, about 20%, about 30%, about 40%, or about 50% of biopolymer. The percentage of biopolymer in the liquid will depend upon the surfactant and/or excipient. For example, in aspects wherein the matrix contains aqueous alcohol, the matrix can comprise up to about 30% biopolymer. In aspects wherein the matrix contains benzyl alcohol or other organic primary solvents, the matrix can comprise up to about 50% biopolymer.

The matrices can be porous or non-porous.

The matrices can further comprise an applicator, which can serve as a substrate for the biopolymer. Exemplary applicators include, but are not limited to, a swab, a pestle, a tape, a spin column, a pad, a fabric, a filter, a membrane, or any other material configured for wiping a surface.

As used herein, "serve as a substrate for" means that the applicator can have the biopolymer exposed on the surface thereof. The applicator, or a portion thereof, can be bound by the biopolymer. The applicator, or a portion thereof, can be coated with the biopolymer. Alternatively, the applicator, or a portion thereof can be made of the biopolymer.

The biopolymers are configured to bind or absorb a biological macromolecule. Biological macromolecules include, but are not limited to, nucleic acids, proteins, polypeptides, peptides, carbohydrates, lipids, compounds having biological activity (such as drug compounds and/or other small molecules that have pharmacokinetic or other biological affects in, for example, a mammal), and combinations thereof. In some embodiments, the biological macromolecule can comprise DNA, RNA, protein, carbohydrate, lipid, small molecule, cellular organic or inorganic component, or a combination thereof. As a biological macromolecule, RNA includes all forms of RNA including, but not limited to, mRNA, rRNA, tRNA, siRNA, miRNA, and hnRNA.

The matrices can bind or absorb an amount of a biological macromolecule of interest that is about 50%, about 60%, about 70%, about 75%, about 80%, about 85%, about 90%, about 91%, about 92%, about 93%, about 94%, about 95%, about 96%, about 97%, about 98%, about 99%, or about 100% of the total biological macromolecule of interest in a biological/test sample.

The biopolymers are configured to be 10% to 100% dissolvable in a chaotropic solvent or an organic solvent dissolve in a solvent and release the biological macromolecule. Upon dissolving, the biological macromolecule is "released," into the solvent (for example, the interaction between the biopolymer and the biological macromolecule is interrupted or broken).

The disclosed matrices can be stable at room temperature (i.e., approximately 70° F.) for prolonged periods, i.e., for at least one day, or for at least one week, or for at least one month, or for at least one year, or for longer than one year.

The disclosed matrices can be used, for example, for separating a biological macromolecule of interest from a mixture of biological macromolecules, for isolating a biological macromolecule of interest from a biological sample, or for isolating a biological macromolecule of interest from a test sample.

Matrix Collectors

Also disclosed are devices for collecting, storing, transporting, and/or processing a biological sample, the devices comprising a tube and a spatula, wherein the tube and the spatula are reversibly connected.

In some embodiments, the tube and the spatula are reversibly connected via a snap break ring, which allows the device to be broken/separated into its component parts (i.e.

the tube and the spatula). When the device is separated along the snap break ring, the tube and the spatula are permanently separated. In some embodiments, the tube and the spatula are reversibly connected via slide-in rings, which allow the device to be separated into its component parts. When the device is separated along the slide-in ring, the tube and the spatula are reversibly separated, and can be later combined to form the device. In some embodiments, the tube and the spatula are reversibly connected via screw-in rings, which allow the device to be separated (unscrewed) into its component parts. When the device is separated along the screw-in ring, the tube and the spatula are reversibly separated, and can be later combined to form the device.

Figure 13A:
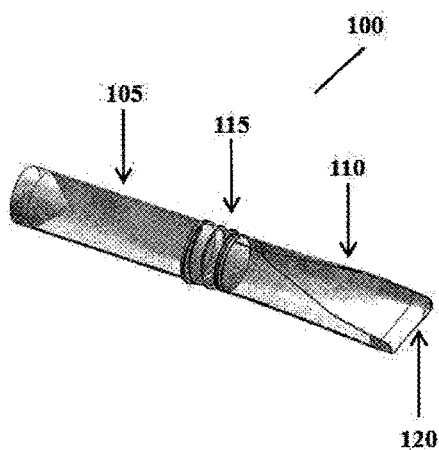
FIG. 13A shows an exemplary screw cap tube matrix sample collector with a breakaway spatula end.
Figure 13B:
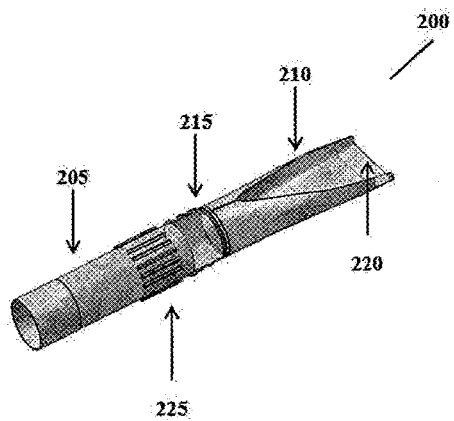
FIG. 13B shows an exemplary screw cap tube matrix sample collector with a slide-in spatula.
Figure 13C:
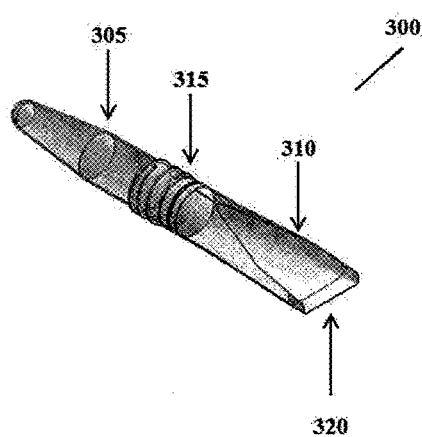
FIG. 13C shows an exemplary conical bottom screw cap tube matrix sample collector with breakaway spatula end.
Figure 13D:
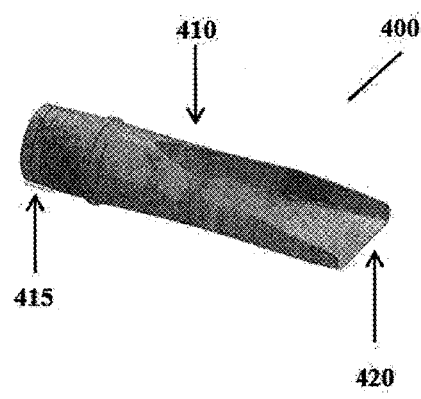
FIG. 13D shows an exemplary matrix sample collector slide-in spatula with straight edge.
Figure 13E:
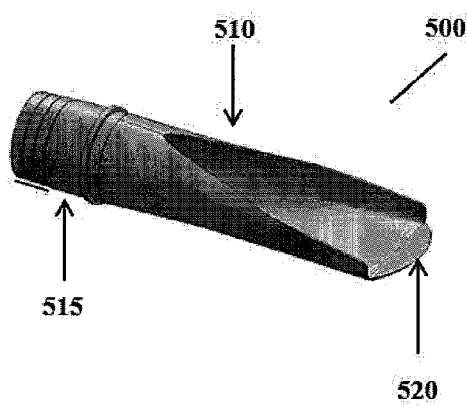
FIG. 13E shows an exemplary matrix sample collector slide-in spatula with round edge.
Figure 13F:
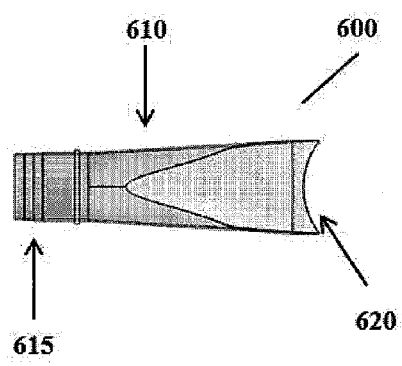
FIG. 13F shows an exemplary matrix sample collector slide-in spatula with concave edge.

Suitable devices for collecting, storing, transporting, and/or processing a biological sample include, but are not limited to, matrix collectors. Exemplary matrix collection spatulas are provided in FIG. 13. Referring to FIG. 13A, a screw cap tube sample collector with a breakaway spatula end (100) is exemplified. The tube (105) and spatula (110) are separated by a snap break ring (115), which allows for disposal of the spatula (110). The spatula (110) has a sharp edge (120). Referring to FIG. 13B, a screw cap tube sample collector with a slide-in spatula (200) is exemplified. The tube (205) and spatula (210) are separated by a snap break ring (215), which allows for disposal of the spatula (210). The spatula (210) has a sharp edge (220). The spatula (210) can slide inside the tube at position (225). Referring to FIG. 13C, a conical bottom screw cap tube sample collector with breakaway spatula end (300) is exemplified. The tube (305) and spatula (310) are separated by a break away ring (315), which allows for disposal of the spatula (310). The spatula (310) has a sharp edge (320). Referring to FIG. 13D, a sample collector slide-in spatula with straight edge (400) is exemplified. The spatula (410) contains slide-in rings (415) and a straight sharp edge (420). The slide-in rings (415) allow the spatula (410) to be connected to a collection tube. Referring to FIG. 13E, a sample collector slide-in spatula with round edge (500) is exemplified. The spatula (510) contains slide-in rings (515) and a round-shaped sharp edge (520). The slide-in rings (515) allow the spatula (510) to be connected to a collection tube. Referring to FIG. 13F, a sample collector slide-in spatula with concave edge (600) is exemplified. The spatula (610) contains slide-in rings (615) and a concave-shaped sharp edge (620). The slide-in rings (615) allow the spatula (610) to be connected to a collection tube.

Suitable materials for manufacturing the device include, but are not limited to, polypropylene, metal, or any other composite plastic material.

The tube is configured to hold a biological macromolecule. Suitable tube sizes include, for example, 1.5 mL, 2 mL, 5 mL, 10 mL, 20 mL, 30 mL, 40 mL, 50 mL, 60 mL, 70 mL, 80 mL, 90 mL, or 100 mL.

The spatula is compatible with the tube, enabling the spatula and tube to be connected to form the device. Suitable spatula sizes include, for example, from about 1 inch to about 20 inches. In some aspects the spatula is 1 inch. In some aspects the spatula is 2.5 inches. In some aspects the spatula is 5 inches. In some aspects the spatula is 7.5 inches. In some aspects the spatula is 10 inches. In some aspects the spatula is 12.5 inches. In some aspects the spatula is 15 inches. In some aspects the spatula is 17.5 inches. In some aspects the spatula is 20 inches.

Devices for Isolating a Biological Macromolecule from a Biological Sample

Also provided are devices for isolating a biological macromolecule from a biological sample, the device comprising: a matrix comprising a biopolymer capable of binding to the biological macromolecule, wherein the biopolymer is about 0% to about 10% dissolvable in water at a pH of about 6 to about 8 and at ambient temperature but is about 10% to 100% dissolvable in a chaotropic solvent or an organic solvent, and wherein the biopolymer is not squid ring teeth protein and a surfactant, excipient, or combination thereof; and an applicator, wherein the applicator serves as a substrate for the matrix.

Any of the matrices, surfactants and excipients, and applicators disclosed above are suitable for use in the disclosed devices.

Methods of Isolating a Biological Macromolecule from a Biological Sample

Also provided are methods of isolating a biological macromolecule from a biological sample, comprising: contacting the biological sample with any of the matrices or devices disclosed herein; incubating the matrix or device in a chaotropic solvent or an organic solvent; and isolating the biological macromolecule.

Any of the matrices, devices, surfactants and excipients, and applicators disclosed above are suitable for use in the disclosed devices.

Exemplary biological macromolecules that can be isolated by the disclosed methods include, but are not limited to, DNA, RNA, protein, carbohydrate, lipid, small molecule, cellular organic or inorganic component, or a combination thereof.

In some embodiments, the methods can further comprise processing the biological macromolecule for analysis. In some aspects, the methods can further comprise processing the biological molecule for genetic fragment analysis. In some embodiments, the methods can further comprise processing the biological molecule for single nucleotide polymorphism (SNP) analysis. In some embodiments, the methods can further comprise processing the biological molecule for Quantitative PCR (real time PCR). In some aspects, the methods can further comprise processing the biological molecule for DNA or RNA amplification analysis. In some aspects, the methods can further comprise processing the biological molecule for DNA or RNA cloning and library preparation. In some aspects, the methods can further comprise processing the biological molecule for small molecule (drug) analysis. In some aspects, the methods can further comprise processing the biological molecule for protein analysis. In some aspects, the methods can further comprise processing the biological molecule for lipid analysis. In some aspects, the methods can further comprise processing the biological molecule for carbohydrate analysis. In some aspects, the methods can further comprise processing the biological molecule for organic analysis. In some aspects, the methods can further comprise processing the biological molecule for inorganic analysis. In some aspects, the methods can further comprise processing the biological molecule for any combination of the above analyses, if suitable for the particular biological macromolecule.

Biological samples include any sample from a subject, including but not limited to humans, non-human mammals, and other animals, that contain, or can contain, a biological macromolecule of interest. Biological samples include, for example, tissue, cell, skin, blood, plasma, serum, urine, saliva, tears, semen, sperm, sweat, cerebrospinal fluid, and other biological fluids, hair, and hair follicles.

The disclosed methods of isolating a biological macromolecule from a biological sample can further comprise collecting the matrix prior to the incubating step. Accordingly, in some embodiments, the methods of isolating a biological macromolecule from a biological sample can comprise:

contacting the biological sample with any of the herein disclosed matrices,
    collecting the matrix,
    incubating the matrix in a chaotropic solvent or an organic solvent, and
    isolating the biological macromolecule.

The collecting step can be performed using any of the matrix collectors described herein (see, for example, the section entitled "matrix collectors").

Methods of Analyzing a Test Sample for the Presence of a Biological Macromolecule Also disclosed are methods of analyzing a test sample for the presence of a biological macromolecule, comprising: contacting the test sample with any of the matrices or device disclosed herein; incubating the matrix or device in a chaotropic solvent or an organic solvent; and analyzing the solvent for the presence of the biological macromolecule.

Any of the matrices, devices, surfactants and excipients, and applicators disclosed above are suitable for use in the disclosed devices.

The disclosed methods can be used to analyze a test sample for a number of biological macromolecules including, but not limited to, DNA, RNA, protein, carbohydrate, lipid, small molecule, cellular organic or inorganic component, or a combination thereof.

Analyzing the solvent for the presence of a biological molecule can comprise genetic fragment analysis, DNA or RNA amplification analysis, DNA or RNA cloning and library preparation, small molecule (drug) analysis, protein analysis, lipid analysis, carbohydrate analysis, organic analysis, inorganic analysis, or any combination thereof.

The biological macromolecule can be extracted and purified from the solvent prior to or after the analyzing.

Test samples include any sample containing a biological macromolecule of interest, including biological samples, as defined elsewhere herein, and non-biological samples, such as liquids, gases, vapors, and solids.

The disclosed methods are suitable for a wide array of analytic applications, including, but not limited to, analysis in conjunction with forensics (such as determining trace amounts of DNA from a crime scene), biometric analysis, genotypic-analysis (such as to determine or predict a trait in an organism), population genetics, human and veterinary medicine (such as for diagnosing or aiding in a diagnosis of a disease, and/or for making a prognosis or treatment recommendation or for staging a diseases), epidemiology, pedigree and breeding analysis, agricultural applications in the animal and plant science areas, water analysis, food analysis (such as for analysis of food safety and the presence or absence of pathogens), paleontology and archeology (such as to determine trace amounts of DNA from such samples), parasitology and other infectious disease analysis, and many other applications wherein determining the presence or absence of a biological macromolecule and/or its characteristics (sequence, for example) would be desirable.

The disclosed methods of analyzing a test sample for the presence of a biological macromolecule can further comprise collecting the matrix prior to the incubating step. Accordingly, in some embodiments, the methods of analyzing a test sample for the presence of a biological macromolecule can comprise:

contacting the test sample with any of the matrices disclosed herein,
    collecting the matrix,
    incubating the matrix in a chaotropic solvent or an organic solvent, and
    analyzing the solvent for the presence of a biological macromolecule.

The collecting step can be performed using any of the matrix collectors described herein (see, for example, the section entitled "matrix collectors").

In a non-limiting illustration of the use of the disclosed matrices, a test sample or biological sample containing a DNA molecule of interest can be contacted with a matrix, which depending on the use of the matrix, can further comprise an applicator. Upon contacting the matrix with the test sample/biological sample containing a DNA molecule of interest, the matrix binds and/or absorbs the DNA molecule of interest. The DNA can be processed to analyze the DNA, such as by determining the sequence of the DNA or genotypic fragment analysis. In some embodiments, the DNA can be analyzed while still bound to/present on the matrix. In preferred embodiments, the DNA can be separated from the matrix by incubating the matrix in a chaotropic solvent or an organic solvent. The sequence of the DNA can be determined to support an inference or conclusion about the source of the sample. The DNA can be amplified, and the amplified DNA can be further analyzed. An exemplary use is illustrated in FIG. 2.

Methods of Isolating a Biological Macromolecule from a Surface Contacted by a Subject Also disclosed are methods of isolating a biological macromolecule from a surface contacted by a subject, comprising contacting a surface that was contacted by a subject with any of the matrices disclosed herein, collecting the matrix, incubating the matrix in a chaotropic solvent or an organic solvent, and analyzing the solvent for the presence of the biological macromolecule. Such methods are referred to herein as "touch DNA" methods, and can be used to recover biological samples, such as epithelial cells, from a surface that was previously touched by the subject.

Any of the matrices, surfactants and excipients, and applicators disclosed above are suitable for use in the disclosed devices.

In some embodiments, the matrix can be configured as a spray. As exemplified in FIG. 3C, for example, a surface that was contacted, or was suspected of being contacted, by a subject can be sprayed with a matrix. The matrix can be collected, incubated in a chaotropic solvent or an organic solvent, and analyzed for the presence of the biological macromolecule.

In some embodiments, the matrix can be configured as a thin layered matrix on sheets of glass, plastic, or any other non-porous surface.

In a non-limiting illustration of the use of the disclosed matrices, a matrix can contact a surface that was previously contacted by a subject. Upon contacting the matrix to the surface, the matrix binds and/or absorbs a biological sample of interest, such as epithelial cells, that was left behind/deposited on the surface. The cells can be processed to analyze the DNA, such as by determining the sequence of the DNA or genotypic fragment analysis. The cells can be separated from the matrix by incubating the matrix in a solvent. The DNA can be isolated and the sequence of the DNA can be determined to support an inference or conclusion about the source of the sample. The DNA can be amplified, and the amplified DNA can be further analyzed. An exemplary use is illustrated in FIG. 3.

Methods of Isolating a Biological Macromolecule from an Exposed Region of a Subject Also disclosed are methods of isolating a biological macromolecule from an exposed region of a subject, comprising contacting any of the herein disclosed matrices to the exposed region of the subject, incubating the matrix in a chaotropic solvent or an organic solvent, and analyzing the solvent for the presence of the biological macromolecule. In some embodiments, the exposed region of the subject is the subject's skin. Such methods are referred to herein as "reverse touch DNA" methods.

DNA biometrics is similar to forensic DNA typing for human identification but the data is used for security purposes including, for example, airport immigration, border control, military intelligence. Invasive methods of sample collection including buccal swab may not be desirable in such settings due to high volume of samples that will require rapid collection and processing, the associated hazards of bodily fluid, swab storage, and the low DNA retrieval. A rapid epithelial cell touch sample (reverse touch DNA) can be collected by a simple touch of the matrix to the expose skin of the hand or wrist, stored dry, and then processed for DNA profiling.

Any of the matrices, surfactants and excipients, and applicators disclosed above are suitable for use in the disclosed devices.

In some embodiments, the matrix can be configured as a spray. As exemplified in FIG. 4, for example, a surface is sprayed with the matrix, and the surface is subsequently contacted to an exposed region of the subject (the subject's finger in FIG. 4C). The matrix can be collected, incubated in a chaotropic solvent or an organic solvent, and analyzed for the presence of the biological macromolecule.

In some embodiments, the matrix can be configured as a liquid. As exemplified in FIG. 5, for example, a matrix in the form of a liquid is contacted to an exposed region of the subject (the subject's hand in FIG. 5). The matrix can be collected, incubated in a chaotropic solvent or an organic solvent, and analyzed for the presence of the biological macromolecule.

In some embodiments, the matrix can be configured as a thin layered matrix on sheets of glass, plastic, or any other non-porous surface. In a non-limiting example of a non-porous surface, the matrix can be configured as a band aid type design as exemplified in FIG. 14. As exemplified in FIG. 14, a matrix in the form of a band aid is contacted to an exposed region of the subject (the subject's hand in FIG. 14). The matrix can be collected, incubated in a chaotropic solvent or an organic solvent, and analyzed for the presence of the biological macromolecule.

The disclosed methods can be used to analyze a test sample for a number of biological macromolecules including, but not limited to, DNA, RNA, protein, carbohydrate, lipid, small molecule, cellular organic or inorganic component, or a combination thereof.

The disclosed methods of isolating a biological macromolecule from an exposed region of a subject can further comprise collecting the matrix prior to the incubating step. Accordingly, in some embodiments, the methods of isolating a biological macromolecule from an exposed region of a subject can comprise:
contacting any of the disclosed matrices to the exposed region of the subject,
collecting the matrix,
incubating the matrix in a chaotropic solvent or an organic solvent, and
analyzing the solvent for the presence of the biological macromolecule.

The collecting step can be performed using any of the matrix collectors described herein (see, for example, the section entitled "matrix collectors") or other suitable devices such as a scraper as shown in FIG. 2E.

In a non-limiting illustration of the use of the disclosed matrices, a matrix can be contacted to an exposed region of a subject, such as the subject's skin. Upon contacting the matrix to the subject, the matrix binds and/or absorbs a biological sample of interest, such as epithelial cells. The cells can be processed to analyze the DNA, such as by determining the sequence of the DNA. The cells can be separated from the matrix by incubating the matrix in a chaotropic solvent or an organic solvent. The DNA can be isolated and the sequence of the DNA can be determined to support an inference or conclusion about the source of the sample. The DNA can be amplified, and the amplified DNA can be further analyzed. An exemplary use is illustrated in FIG. 4, FIG. 5, and FIG. 14.

Kits

Disclosed herein are kits comprising any of the above disclosed matrices. In some embodiments, the kit can further comprise one or more reagents for sample collection and/or sample processing. In some embodiments, the kit can further comprise instructions for using the matrix.

EXAMPLES

The following examples are provided to further describe some of the embodiments disclosed herein. The examples are intended to illustrate, not to limit, the disclosed embodiments.

Biopolymer Selection

A sterile cotton swab matrix is most commonly used for collection of biological macromolecule for forensic analysis. The cotton swab is simple to use, inexpensive, and can be used for a wide range of biological samples (e.g., saliva, blood) and surfaces (e.g., wood, metal, fabric). Other swab types (e.g., foam, nylon) can also be used depending on the sample type and surface. The sampling efficiency (biological macromolecule capture from a biological sample) and extraction efficiency (yield of biological macromolecule release) of collection devices often differ, thereby resulting in a loss of valuable material required for downstream analysis. At least 100-200 picograms (~20-40 cells) of extracted DNA is required for forensic DNA typing, thus inefficient sample recovery from a surface or cell entrapment within swab fibers is particularly problematic for forensic samples where the amount of recoverable material is at trace levels. This issue is further compounded by inefficiencies encountered with the methods commonly employed by forensic laboratories to extract DNA from human cells.

Various biopolymers (proteins and polysaccharides) were initially selected based on their insolubility in water at biological pH and their ability to be readily made soluble in extraction and purification procedures for nucleic acids (DNA & RNA), biological materials and small molecules.

The solubility of various swab matrices in water and 7M G-HCl where compared (Table 1). The matrices listed in Table 1 were soaked in water or 7M G-HCl (guanidine hydrochloride) to ascertain solubility. HPMC, starch, avenin, gliadin, secalin, horedein, zein, soy prolamin, flax prolamin, kafirin, hemp, coffee legumin, casein, and gelatin were readily solubilized in 7M G-HCl, whereas the other matrices tested were insoluble in 7M G-HCl (data not shown). Zein was selected as a representative of prolamin proteins.

TABLE 1

Select Biopolymers

|  | Source | Solubility in Water | 7M G-HCl | Notes |
|---|---|---|---|---|
| Polysaccharides |  |  |  |  |
| Cellulose | Plant | No | No | Composite material |
| Hydroxypropyl methyl cellulose (HPMC) | Plant | Yes, colloid | Yes, colloid fluid | Composite material |
| Starch | Plant (potato, rice wheat) | No | Yes colloid | Composite material |
| Proteins |  |  |  |  |
| Avenin | Oat | No | Yes | Matrix material |
| Gliadin | Wheat | No | Yes | Matrix material |
| Secalin | Rye | No | Yes | Matrix material |
| Horedein | Barley | No | Yes | Matrix material |
| Zein (Prolamin) | Corn | No | Yes | Matrix material |
| Soy Prolamin | Soy flour | No | Yes | Composite material |
| Flax Prolamin | Flax Seed flour | No | Yes | Composite material |
| Kafirin | *Sorghum* | No | Yes | Matrix material |
| Hemp | Hemp flour | No | Yes | Composite material |
| Coffee Legumin | Coffee powder | No | Yes | Composite material |
| Casein | Bovine Milk | No | Yes | Extruded as fibers |
| Gelatin | Bovine | Partial, slowly | Yes | Composite material |
| Collagen | Bovine | Partial | Partial | Matrix material |

To aid in absorption, the protein and polysaccharides were mixed with surfactants and excipients to impart specific properties such as hygroscopicity, hydrophilicity, and colloidal swelling upon contact with aqueous solutions. Exemplary surfactants and excipients include glycerol, Sodium Dodecyl Sulfate (SDS), sodium stearate, glyceryl laurate (1-Monolaurin), Polysorbate 20 (polyoxyethylene (20) sorbitan monolaurate; Tween 20), sodium cholate, sodium deoxycholate, DDPS (DPS) N-Dodecyl-N,N-dimethyl-3-ammonio-1-propanesulfonate, 3-(N,N-dimethyl myristyl ammonio) propanesulfonate (TPS), polyoxyethylene (20) cetyl ether (Brij® C10), ethanol, PEG 7000-9000, polyvinyl alcohol, monolaurin.

Dissolvable Sample Collection Matrix Preparation

Based on the initial results with zein, gelatin, and starch, matrices (in the form of swabs and films) were prepared with these biopolymers and various composites and surfactants to impart specific hydrophilic, hygroscopic and colloidal properties. Table 2 lists the solutions prepared for use as swab and film matrix.

TABLE 2

Exemplary Matrices

| Code | Matrix Description |
|---|---|
| Z or Z20 | 20% Zein in 75% aqueous ethanol |
| Z30 | 30% Zein in 75% aqueous ethanol |
| Z50 | 50% Zein in 75% aqueous ethanol |
| A | 20% Zein in 75% aqueous ethanol and 2% glycerol |
| B | 20% Zein in 75% aqueous ethanol and 10% PEG 7000-9000 |
| C | 20% Zein in 75% aqueous ethanol and 10% polyvinyl alcohol |

TABLE 2-continued

Exemplary Matrices

| Code | Matrix Description |
|---|---|
| D | 20% Zein in 75% aqueous ethanol and 10% gelatin |
| E | 20% Zein in 75% aqueous ethanol and 4% Monolaurin |
| F | 20% Zein in 75% aqueous ethanol and 1% sodium Stearate |
| G | 20% Zein in 75% aqueous ethanol and 1% SDS |
| H | 20% Zein in 75% aqueous ethanol and 2% sodium Stearate |
| J | 20% Zein in 75% aqueous ethanol and 2% SDS |
| K | 20% Zein in 75% aqueous ethanol, 2% SDS and 10% glycerol |
| L | 20% Zein in 75% aqueous ethanol, 1% SDS and 10% glycerol |
| M | 20% Zein in 75% aqueous ethanol, 2% SDS and 20% glycerol |
| N | 20% Zein in 75% aqueous ethanol, 10% glycerol, 2% SDS and 1% Starch |
| O | 20% Zein in 75% aqueous ethanol and 10% glycerol |
| Q | 20% Zein in 75% aqueous ethanol, 10% glycerol and 2% trehalose |
| QS | 20% Zein in 75% aqueous ethanol, 10% glycerol, 2% trehalose and 2% SDS |
| O10 | 10% Zein in 85% aqueous ethanol and 5% glycerol |
| L10 | 10% Zein in 85% aqueous ethanol, 0.5% SDS and 5% glycerol |
| Q10 | 10% Zein in 85% aqueous ethanol, 5% glycerol and 1% trehalose |
| Q11 | 10% Zein in 85% aqueous ethanol, 10% glycerol and 1% trehalose |
| K10 | 20% Zein in 85% aqueous ethanol, 1% SDS and 5% glycerol |
| ZD10 | 14% Zein in 85% aqueous ethanol and 2% sodium deoxycholate |
| ZD11 | 16% Zein in 80% aqueous ethanol and 2% sodium deoxycholate |
| ZS11 | 16% Zein in 80% aqueous ethanol and 2% SDS |
| PD10 | 16% Zein in 80% aqueous ethanol, 2% sodium deoxycholate and 10% glycerol |
| K105 | 10% Zein in 75% aqueous ethanol, 0.5% SDS and 10% glycerol |
| K102 | 14% Zein in 75% aqueous ethanol, 0.5% SDS and 10% glycerol |
| K103 | 16% Zein in 75% aqueous ethanol, 1.62% SDS and 8% glycerol |
| K5 | 5% Zein in 75% aqueous ethanol, 1% SDS and 5% glycerol |
| K2 | 2% Zein in 75% aqueous ethanol, 1% SDS and 2% glycerol |
| K1 | 1% Zein in 75% aqueous ethanol, 1% SDS and 1% glycerol |
| QD10 | 16% Zein in 85% aqueous ethanol, 10% glycerol, 2% trehalose and 2% Sodium deoxycholate |
| Ave | Avenin (Oat); 20% in 85% aqueous ethanol |
| Ave2 | Avenin2 (Oat); 20% in 85% aqueous ethanol |
| Gli | Gliadin (Wheat); 20% in 85% aqueous ethanol |
| Sec | Secalin (Rye); 20% in 85% aqueous ethanol |
| Hor | Horedein (Barley); 20% in 85% aqueous ethanol |
| Soy | Soy seed Prolamin & Cupin; 20% in 85% aqueous ethanol |
| Flx | Flax Seed Flour Cupin; 20% in 85% aqueous ethanol |
| Hmp | Hemp flour Prolamin; 20% in 85% aqueous ethanol |
| Cof | Coffee Legumin; 20% in 85% aqueous ethanol |
| Kaf | Kafirin (*Sorghum*); 20% in 85% aqueous ethanol |

Swab Preparation

A plastic pestle shaped swab was dipped in selected zein matrix solution and allowed to dry overnight. Each stick was coated with 3-5 layers of solution. The total thickness of the layers was approximately 1-3 mm.

Film Preparation

The various matrices listed in Table 2 were sprayed on glass for reverse touch DNA and DNA Biometric sampling. Any appropriate matrix can be used to create a film of the matrix.

Blood Dilution

To achieve the appropriate DNA concentration and number of cells to mimic trace DNA field sampling conditions, various blood dilutions were prepared as shown in Table 3.

TABLE 3

Blood Dilutions and Cell Count

| Code | Source | Yield Average | Cells (WBC in blood) |
|---|---|---|---|
| A | 2 µL Whole blood | 75 ng | 10,000 cells |
| B | 2 µL diluted blood 1:10 | 7 ng | 1000 cells |
| F | 2 µL diluted blood 1:100 | 700 pg | 100 cells |
| J | 2 µL diluted blood 1:200 | 350 pg | 50 cells |
| | Trace DNA, Touch & Skin | | |
| S | Skin | 200 pg | 10-25 cells |
| T | Touch | 100 pg | 10-15 cells |
| rT | Reverse Touch | 100 pg | 10-15 cells |

Trace DNA (Finger print) is usually less than 100 pg (~17 cells). 100 pg can be used as the threshold limit.

Contacting the Matrix to a Biological Sample

Figure 2A:
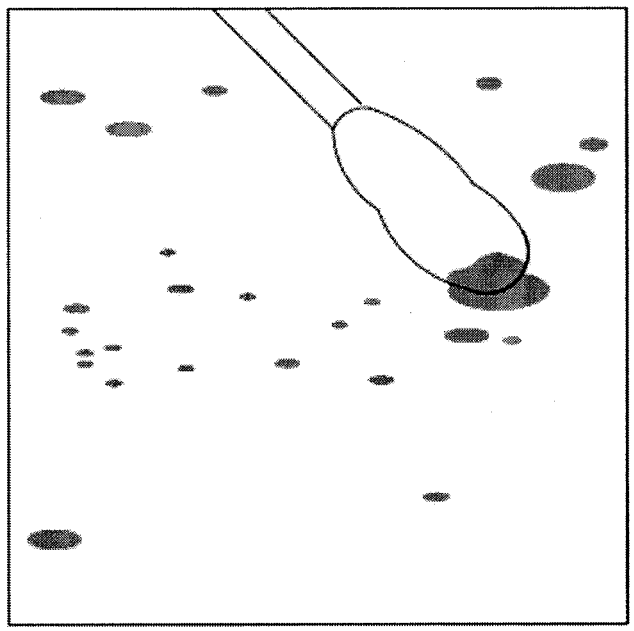
FIG. 2A shows blood sampling using a cotton swab.
Figure 2B:
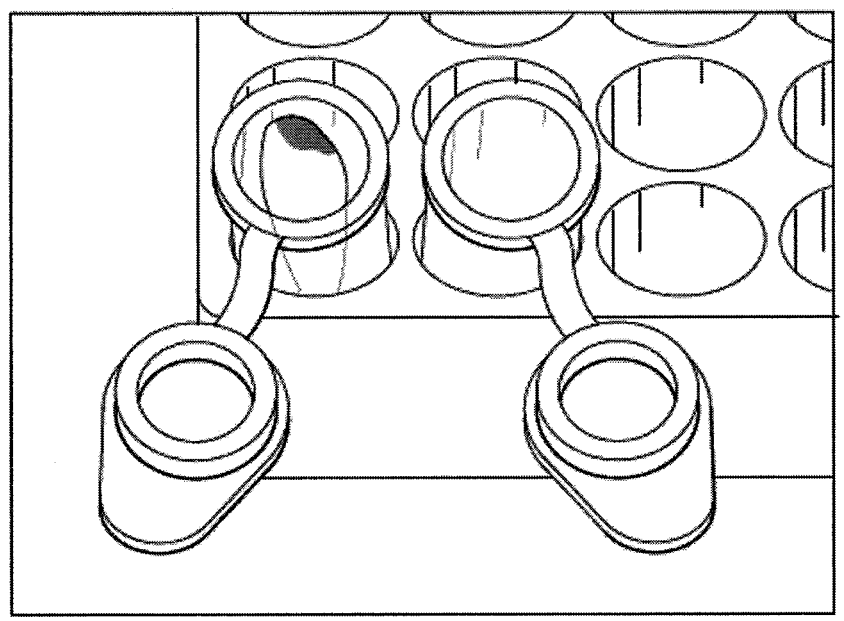
FIG. 2B shows a cotton swab saved for DNA extraction.

FIG. 2A-FIG. 2F illustrates an example of blood sampling (the same procedure can be used for saliva, semen, sweat, tear or any other bodily fluid). FIG. 2A—the classic sample collection using a swab and FIG. 2B—the swab was saved for DNA processing. FIG. 2C—The matrix in liquid form was applied on all the spots that were to be collected for sample processing. Varying amounts of the matrix was applied to cover the sample spots. The matrix was allowed to dry for 3-5 minutes. FIG. 2D—Blood dilutions as listed in Table 3 were spotted on plastic plates and allowed to dry. The matrix was then applied to each spot and allowed to dry. FIG. 2E—The dried matrix film was picked up and FIG. 2F—transferred to a tube for DNA processing.

Touch and Reverse Touch DNA Sampling

Figure 3A:
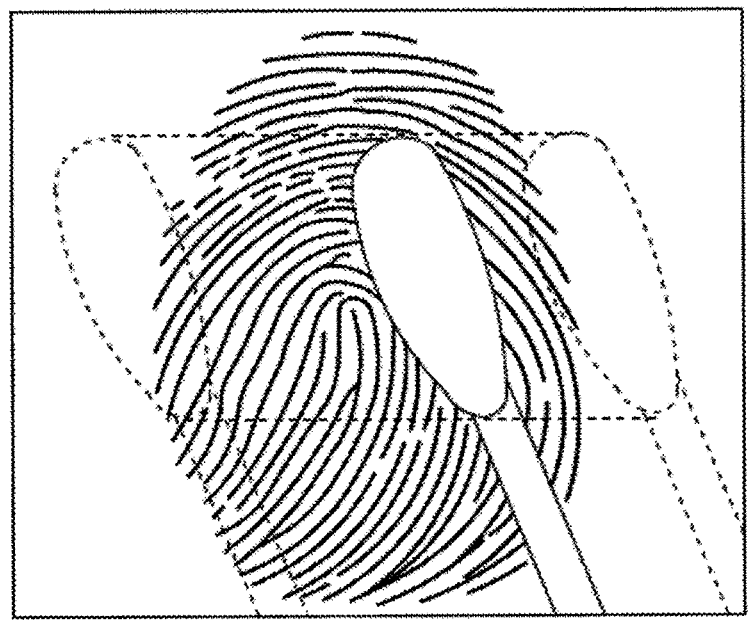
FIG. 3A shows fingerprint epithelial cell sampling using a cotton swab.
Figure 3B:
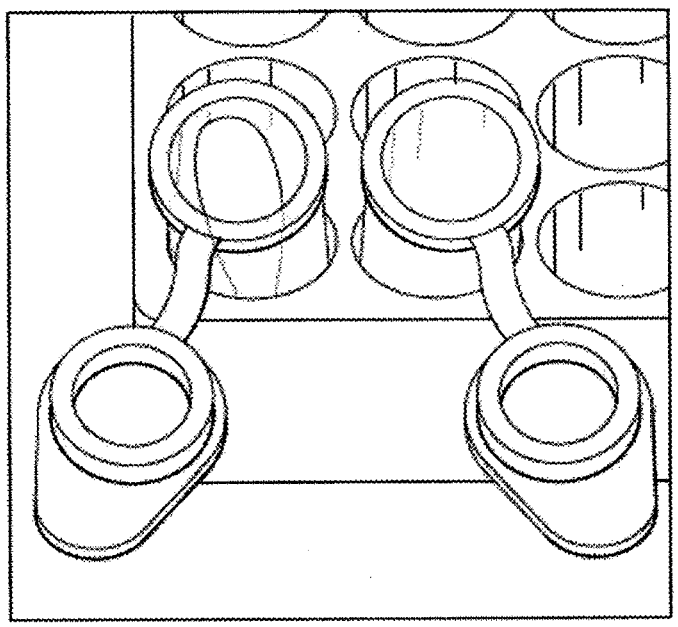
FIG. 3B shows a cotton swab saved for DNA extraction.
Figure 3C:
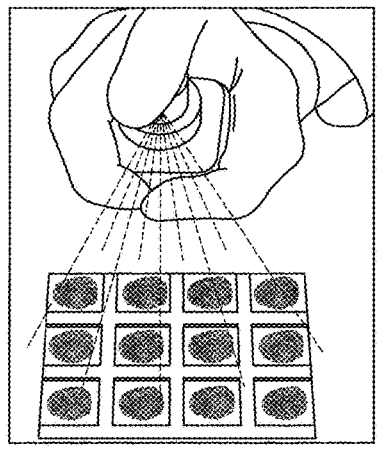
FIG. 3C shows a surface that was, or is suspected of being, previously contacted by a subject. The surface is sprayed with exemplary biopolymer matrix to create a dried exemplary biopolymer matrix film.
Figure 3D:
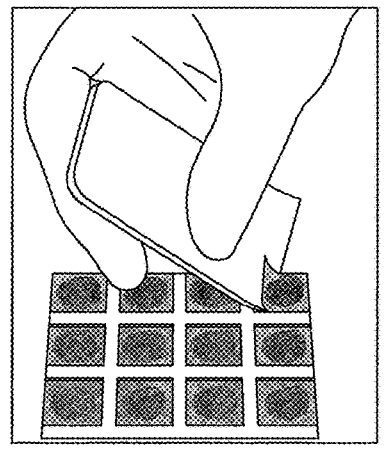
FIG. 3D and FIG. 3E show dried exemplary biopolymer matrix film collected for DNA extraction.
Figure 3E:
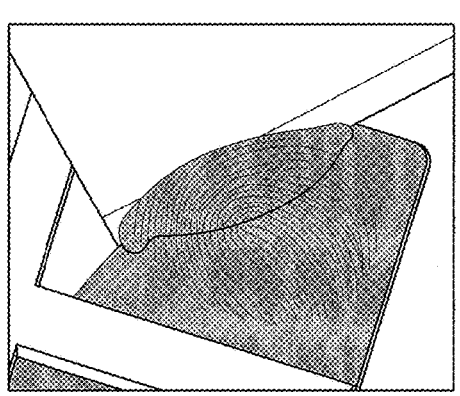
Figure 3F:
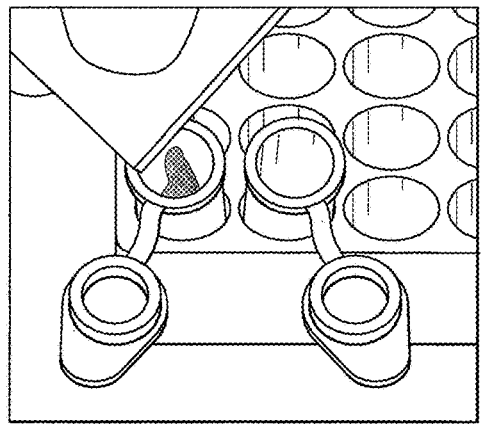
FIG. 3F shows dried exemplary biopolymer matrix film transferred to a tube for DNA extraction.

FIG. 3A-FIG. 3F illustrates touch DNA sampling performed from an area believed to have been in contact with human skin and thus possibly having shed epithelial cells. FIG. 3A—Graphically shows the fingerprint contact area and swabbing of the area. FIG. 3B—The swab was stored and processed for DNA extraction. FIG. 3C—The suspected area of contact was sprayed with an exemplary matrix (K105) and allowed to dry for 3-5 minutes. FIG. 3D & FIG. 3E—The matrix was scrapped. FIG. 3F—The scraped dried matrix was collected in a tube for DNA processing.

Figure 4A:
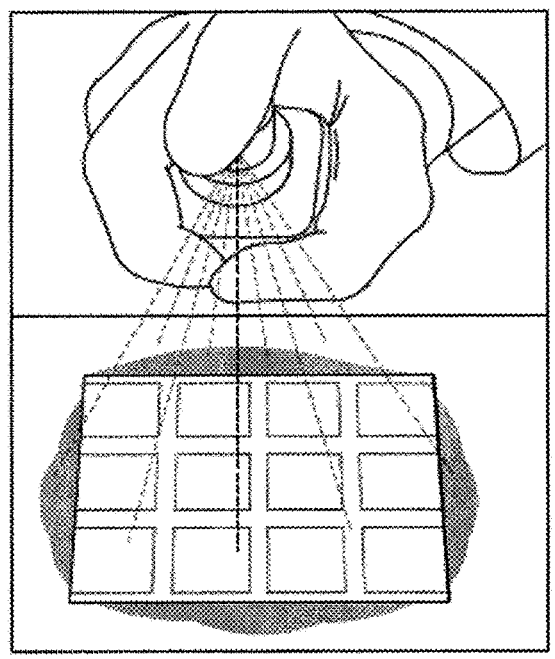
FIG. 4A shows a glass plate sprayed with exemplary biopolymer matrix.
Figure 4B:
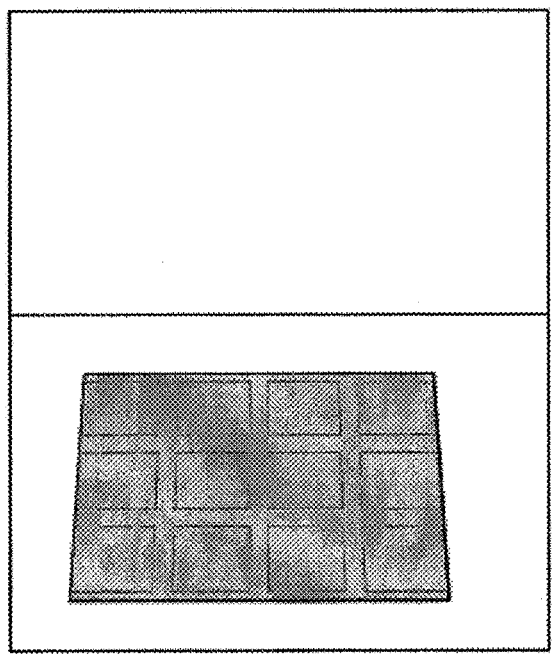
FIG. 4B shows the exemplary biopolymer matrix dried on the glass plate to create a dried exemplary biopolymer matrix film.
Figure 4C:
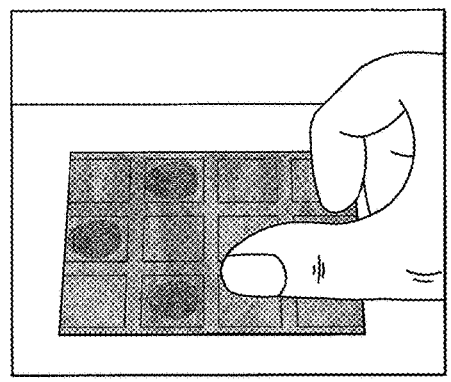
FIG. 4C shows a thumb contacting a dried exemplary biopolymer matrix film on a glass plate.
Figure 4D:
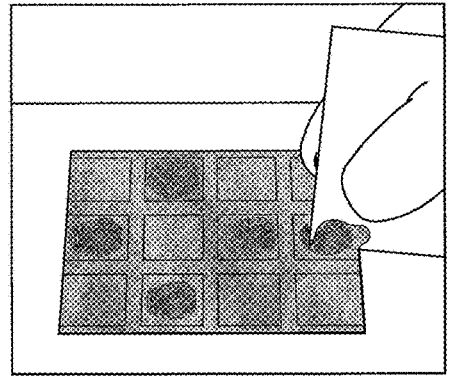
FIG. 4D shows dried exemplary biopolymer matrix film collected for DNA extraction.
Figure 4E:
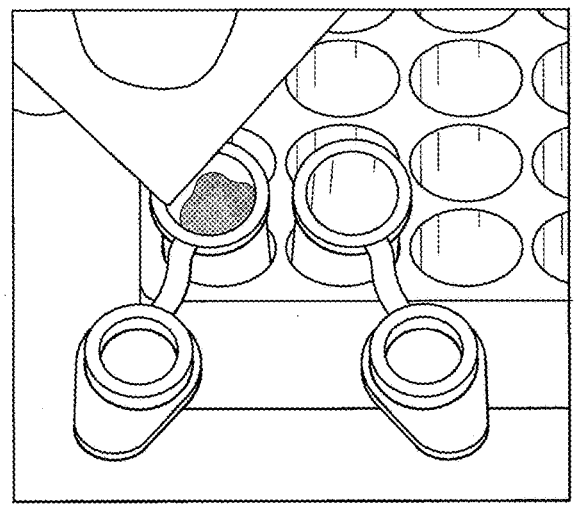
FIG. 4E shows dried exemplary biopolymer matrix film transferred to a tube for DNA extraction.

Referring to FIG. 4A-FIG. 4E, a touch sample was acquired by touching a dried film of the matrix. FIG. 4A—The matrix was sprayed on a controlled surface, e.g. glass plate, and FIG. 4B—the matrix K105 was allowed to dry. FIG. 4C—The subject made finger contact with the dried matrix film on a predetermined marked area of approximately 1 square cm for 3-5 seconds. FIG. 4D—The touched marked area was scraped to lift the matrix film. FIG. 4E—The collected matrix was transferred to a tube for DNA processing.

Figure 5A:
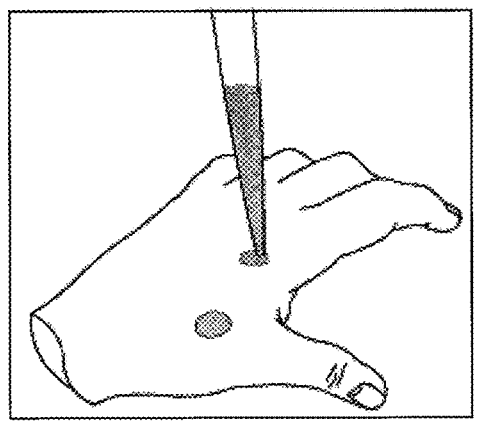
FIG. 5A shows exemplary biopolymer matrix in liquid form applied to skin on the back of a hand.
Figure 5B:
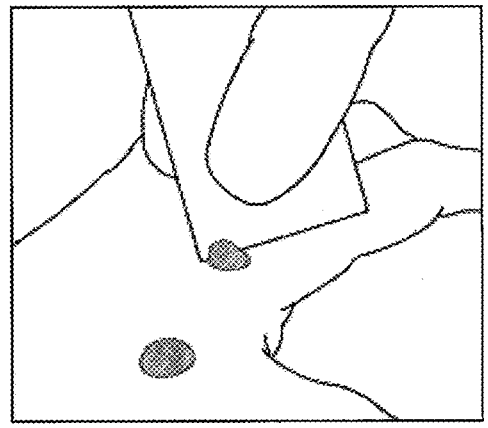
FIG. 5B shows dried exemplary biopolymer matrix film collected for DNA extraction.
Figure 5C:
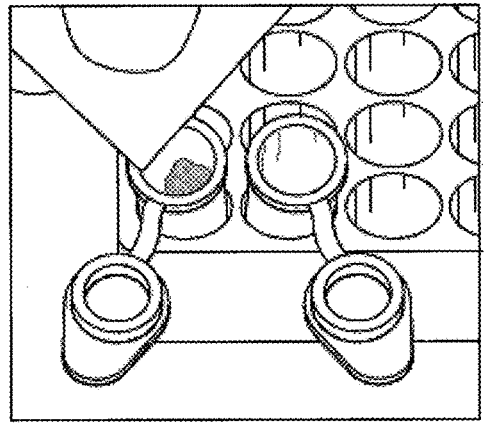
FIG. 5C shows dried exemplary biopolymer matrix film transferred to a tube for DNA extraction.

FIG. 5A-FIG. 5D illustrates an exemplary skin lift procedure, wherein a matrix in the form of a liquid was applied to a subject. FIG. 5A & FIG. 5B—The matrix Z20 solution (5 µL) was applied to an open, accessible, and appropriate area of the skin and was allowed to dry. The matrix dried in about 3-5 minutes. FIG. 5C—The dried matrix was lifted and FIG. 5D—transferred to a tube for DNA processing. All DNA extractions were performed using Gene Link Omni-Mag DNA purification system (OM) (Catalog #: 40-4100-01) (as described in the "DNA extraction from the matrices" section herein), unless otherwise indicated.

Figure 14A:
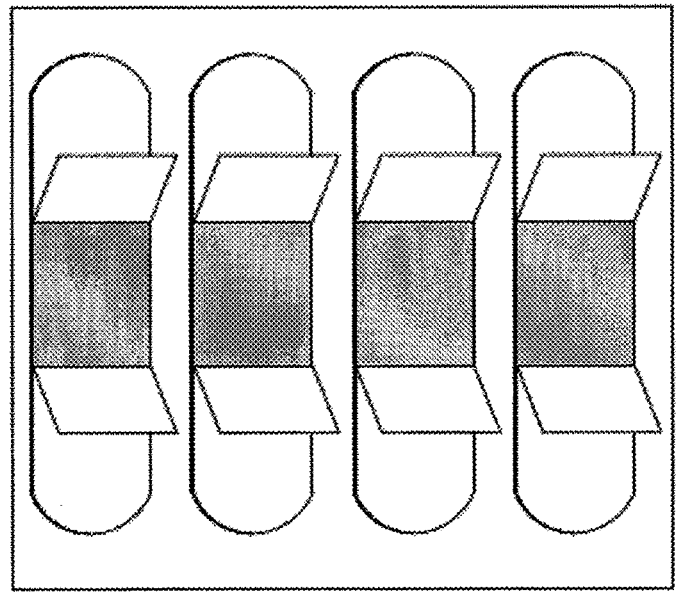
FIG. 14A shows an exemplary biopolymer matrix film formed on a non-porous substrate for exemplary reverse touch DNA sampling.
Figure 14B:
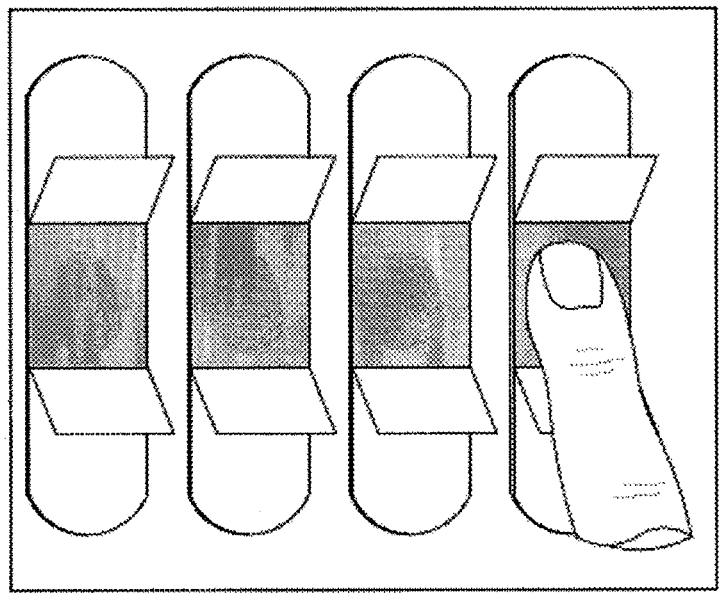
FIG. 14B shows a finger contacting an exemplary biopolymer matrix film on a non-porous substrate.
Figure 14C:
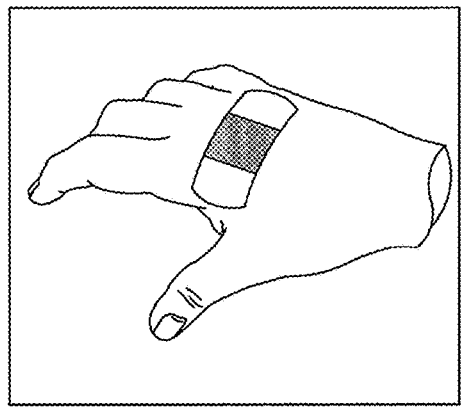
FIG. 14C shows a non-porous substrate containing an exemplary biopolymer matrix film applied to skin on the back of a hand.
Figure 14D:
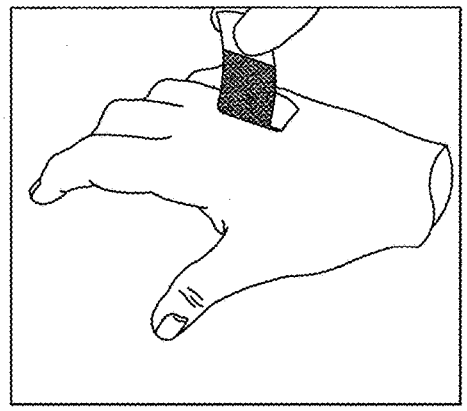
FIG. 14D shows a non-porous substrate containing an exemplary biopolymer matrix film removed from skin on the back of a hand.
Figure 14E:
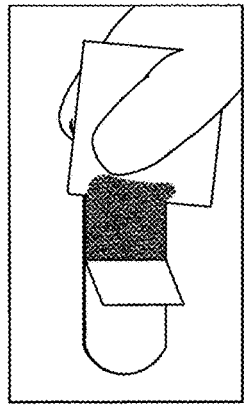
FIG. 14E shows dried exemplary biopolymer matrix film collected for DNA extraction.
Figure 14F:
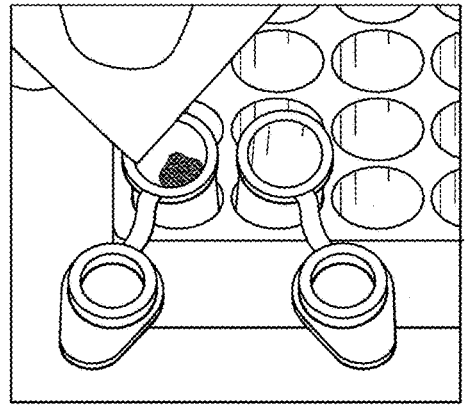
FIG. 14F shows dried exemplary biopolymer matrix film transferred to a tube for DNA extraction.

FIG. 14A-FIG. 14F illustrates an exemplary reverse touch sample collection procedure for clinical and biometric analysis, wherein a matrix in the form of a band aid was applied to a subject. The matrix was in a thin sheet formed on a suitable non-porous substrate (FIG. 14A) that was touched by a finger or exposed surface of the subject's skin (FIG. 14B, FIG. 14C). The matrix was removed (FIG. 14D), scrapped (FIG. 14E), and transferred to a tube (FIG. 14F) for DNA processing.

DNA Extraction from the Matrices

DNA Extraction was performed by using Gene Link Omni-Clean System (catalog #: 40-4130-10) (described below) and three different kits for comparison following the manufacturer's protocol: Gene Link Omni-Mag DNA purification system (Catalog #: 40-4100-01) (described below); ABI-ThermoFisher PrepFiler® (PF) (catalog#: 4463351) (described below); and Promega DNA-IQ System (PM) (Catalog #: DC-6701) (described below). Briefly, blood dilutions were applied and collected as illustrated in FIG. 2, panels D-F. The collected samples were processed for DNA extraction using kits listed above and following the kit manufacturer's protocol.

Gene Link Omni-Mag DNA Purification System (Catalog #: 40-4100-01)—

Manufacturer instructions were followed as briefly described below. The swab or other matrix was placed into a spin basket 1.5 mL eppendorf tube. 300 µL Omni-Mag™ Lysis Buffer (4 M guanidine thiocyanate; referred to as "OCC-3") containing 10 mM DTT, was added to the tube, which was vortexed vigorously and incubated at 60° C. for 30 min. The tube was vortexed again and cooled to ambient temperature. The tubes were centrifuged for 30 seconds at 5K rpm. The spin basket containing the swab or other sold matrix substrate was discarded. 7 µL of Omni-Mag™ PMP (Paramagnetic particles) were added to the tubes, and the tubes were vortexed vigorously every minute for five minutes, then centrifuged briefly. The tubes were placed on a magnetic stand and the solution was removed using a pipette, taking care not to disturb the magnetic particles. 150 µL of Omni-Mag™ Lysis Buffer (OCC-3) containing DTT was added to the tubes, which was vortexed and returned to the magnetic stand. The solution was removed using a pipette, taking care not to disturb the magnetic particles. 350 µL of 1×G3-DNA Wash solution (50 mM Tris-HCl pH 7.5, 100 mM NaCl and 10 mM EDTA) was added to the tubes, which were vortexed vigorously and centrifuged briefly. The tubes were placed on the magnetic stand and the solution was discarded, taking care not to disturb the magnetic particles. Another 350 µL of 1×G3-DNA Wash solution was added to the tubes, which were vortexed vigorously and centrifuged briefly. The tubes were placed on the magnetic stand and the solution was discarded, taking care not to disturb the magnetic particles. The tubes were allowed to air-dry for 5 minutes at room temperature. 50 µL of DNA Elution Buffer (10 mM Tris-HCl pH 8.0 and 0.1 mM EDTA pH 8.0) (Low TE) was added to the tubes, which were vortexed vigorously and incubated for 20 min at 60° C. The tubes were vortexed and centrifuged briefly, and placed on the magnetic stand. The DNA solution was transferred to a new microcentrifuge tube. If the subsequent analysis of the DNA required higher concentrations, the sample was evaporated in a speedvac to a smaller volume. Promega DNA-IQ System (PM) (Catalog #: DC-6701)—Manufacturer instructions were followed as briefly described below. The sample was placed in a ClickFit Microtube (Promega Cat.#V4741) and the appropriate volume of Lysis Buffer was added (see Column 2 of Table 1 of the manufacture instructions for the appropriate volume to add). The lid was closed and the tube was incubated at 70° C. for 30 minutes. The tube was removed from the heat source, centrifuged, and the sample was transferred to a DNA IQ™ Spin Basket seated in a new ClickFit Microtube. The tube was centrifuged at room temperature for 2 minutes at maximum speed in a microcentrifuge. The spin basket was removed. 7 µl of DNA IQ™ Resin was added to the sample. The sample was vortexed for 3 seconds at high speed, and incubated at room temperature for 5 minutes, during which time the tube was vortexed for 3 seconds once every minute. The tube was vortexed for 2 seconds at high speed and placed in the magnetic stand. The solution was removed and discarded without disturbing the resin pellet. 100 µl of prepared Lysis Buffer was added, the tube was removed from the magnetic stand, and vortexed for 2 seconds at high speed. The tube was returned to the magnetic stand and the Lysis Buffer was removed and discarded. 100 µl of prepared 1× Wash Buffer was added, the tube was removed from the magnetic stand, and vortexed for 2 seconds at high speed. The tube was returned to the magnetic stand and the wash buffer was removed. 100 µl of prepared 1× Wash Buffer was again added, the tube was removed from the magnetic stand, vortexed for 2 seconds at high speed, returned to the magnetic stand, and the wash buffer was removed. 100 µl of prepared 1× Wash Buffer was again added, the tube was removed from the magnetic stand, vortexed for 2 seconds at high speed, returned to the magnetic stand, and the wash buffer was removed. The resin was allowed to allowed to air dry on the magnetic stand for 5 minutes. 100 µl of Elution Buffer was added, the tube was vortexed for 2 seconds at high speed, and incubated at 65° C. for 5 minutes. The tube was removed from the heat source, vortexed for 2 seconds at high speed, and immediately placed the on the magnetic stand. The DNA-containing solution was removed and saved for later use/analysis.

ABI-ThermoFisher PrepFiler® (PF) (Catalog#: 4463351)—

Manufacturer instructions were followed as briefly described below. The sample was placed in a PrepFiler® Spin Tube or standard 1.5-mL microcentrifuge tube. 300 µL PrepFiler® Lysis Buffer (see manufacturer protocol) and 3 µL 1.0 M DTT were added to the tube. The tube was capped, vortexed for 5 seconds, and centrifuged briefly. The tube was placed in a thermal shaker, incubated at 70° C. and 900 rpm (see manufacturer protocol for appropriate times). Sample substrate, if present, was removed, and the tube was centrifuged for 2 seconds to collect the condensate from the tube cap. A PrepFiler® Filter Column was inserted into a new 1.5-mL PrepFiler® Spin Tube and the sample tube contents were carefully transferred into the filter column. The filter column/spin tube was capped and centrifuged at the maximum g of the centrifuge (for example, 2 minutes at 12,000 to 14,000 rpm or 5 minutes at 3,000 to 4,000 rpm). If the volume in the tube was less than 180 µL, the filter column/spin tube was centrifuged for an additional 5 minutes. The filter column was removed from the spin tube and the filter column was discarded.

PrepFiler® Magnetic Particles tube approximately was vortexed for 5 seconds, inverted to confirm that no visible pellet remained in the bottom of the tube, then centrifuged briefly. 15 µL of magnetic particles were pipetted into the tube containing the sample lysate. The sample lysate tube was capped, vortexed it at low speed (approximately 500 to 1,200 rpm) for 10 seconds, then centrifuged briefly. 180 µL of isopropanol was added to the sample lysate tube, the tube was capped, vortexed it at low speed (approximately 500 to 1,200 rpm) for 5 seconds, then centrifuged briefly. The sample lysate tube was placed in a shaker or on a vortexer (with adaptor) and mixed at room temperature at 1,000 rpm for 10 minutes.

The sample DNA tube was vortexed at maximum speed (approximately 10,000 rpm) for 10 seconds, then centrifuged briefly. The sample DNA tube was placed in a magnetic stand and, when the size of the pellet stopped increasing (approximately 1 to 2 minutes), the liquid phase was removed and discarded. The pellet was washed three times as follows:

Wash buffer was added to the sample DNA tubes, the tubes were capped and removed from the magnetic stand.

The tube was vortexed at maximum speed (approximately 10,000 rpm) until there was no visible magnetic particle pellet on the side of the tube (approximately 5 seconds), then centrifuged briefly.

The tube was placed in the magnetic stand for 30 to 60 seconds and the liquid was removed and discarded.

After three washes, the tube was opened and allowed to air-dry for 7 to 10 minutes.

50 µL of PrepFiler® Elution Buffer was added to the tube. The tube was capped, vortexed it at maximum speed (approximately 10,000 rpm) until there was no visible magnetic particle pellet on the side of the tube (approximately 5 seconds), then centrifuged briefly. The tube was placed in a thermal shaker and incubated at 70° C. and 900 rpm for 5 minutes. The tube was vortexed at maximum speed (approximately 10,000 rpm) until there was no visible magnetic particle pellet on the side of the tube (approximately 2 seconds), then centrifuged briefly. The tube was placed in the magnetic stand and incubated until the size of the pellet at the side of the tube stopped increasing (at least 1 minute). The liquid from the tube (which contains the isolated genomic DNA) was transferred to a new spin tube or 1.5-mL microcentrifuge tube for further analysis/processing.

Gene Link Omni-Clean System (Catalog #: 40-4130-10)—

Manufacturer instructions were followed as briefly described below. The volume of solution containing DNA to be concentrated was determined. Two volumes of OCC-2 was added to the solution and was mixed. Glass bead solution was mixed by vortexing and the glass bead solution was added to the DNA solution (5 µl of glass beads is sufficient to bind 5 µg of DNA. For solutions containing more than 5 µg of DNA, an additional 1 µl of glass bead solution was added for each additional 1 µg of DNA). The sample was vortexed and incubated on ice for 5 minutes, mixing occasionally. The sample was centrifuged at 4K rpm for 30 seconds and the supernatant was discarded. The glass bead pellet was resuspended in 400 µl of Omni-Clean™ G3 DNA wash solution (50 mM Tris-HCl pH 7.5, 100 mM NaCl and 10 mM EDTA) using a pipette. The resuspended pellet was centrifuged at 4K rpm for 30 seconds and wash 2 more times with the same volume of Omni-Clean™ G3 DNA wash solution. After removing the final wash solution, the tube was centrifuged and the residual alcohol was removed with a pipette. The tubes were incubated with the caps open for 10 minutes to allow the alcohol to evaporate. The pellet was resuspended in at least 10-20 µl of hot (~55° C.) sterile water or low salt buffer (TE) by vortexing, and was centrifuged for 30 seconds at 6K RPM. The supernatant, which contained the eluted DNA, was recovered. The pellet was again resuspended in at least 10-20 µl of hot (~55° C.) sterile water or low salt buffer (TE) by vortexing, was centrifuged for 30 seconds at 6K RPM, and the supernatant, which contained the eluted DNA, was recovered.

DNA Amplification—Fragile X CGG Triple Repeat Region

DNA was extracted using Gene Link Omni-Clean System (catalog #: 40-4130-10) (as described previously herein) and extraction compared with either 2M guanidine thiocyanate, 3.5 M guanidine HCl, 0.5M NaCl and 0.1M phosphate buffer pH 6.5 (referred to as "OCC-1") or 7M guanidine HCl (referred to as "OCC-2"). Following elution in 10 µL of water, 2 µL aliquots were used to perform PCR amplification (FIG. 1). The extracted DNA samples were analyzed by PCR amplification using Gene Link™ Fragile X GScan™ Kit (Gene Link™ Catalog#: 40-2004-15) following the manufacturer's protocol. Briefly, 18 µL of PCR premix-PP (described below) and 1 µL DNA Template (~100 ng for chromosomal DNA) were added to each sample. The PCR premix-PP contained the following amounts and components per reaction:

5 µL sterile water;
4 µL GLFX GScan™ Component L;
10 µL GLFX GScan™ Component E; and
2 µL GLFX GScan™ Component D.

The tubes were transferred to a thermal cycler and the "hot start" program was run as follows:

Denaturation: 5 minutes at 98° C. for 1 cycle
Hold—62° C.

2 µL of Taq enzyme mix was added during the hold. The Taq enzyme mix contained the following components: 2 µL of PCR premix-PP and 0.25 2 µL Taq polymerase. The amplification was performed using the following conditions.

| Step | Time and Temperature | Cycles |
| --- | --- | --- |
| Denaturation | 2 minutes at 94° C. | 1 |
| Denaturation | 30 seconds at 94° C. | 30 |
| Annealing | 30 seconds at 60° C. | |
| Extension | 3 minutes at 72° C. | |
| Fill up | 7 minutes at 72° C. | 1 |
| Hold | Hold for infinity at 4° C. | Hold |

Figure 1B:
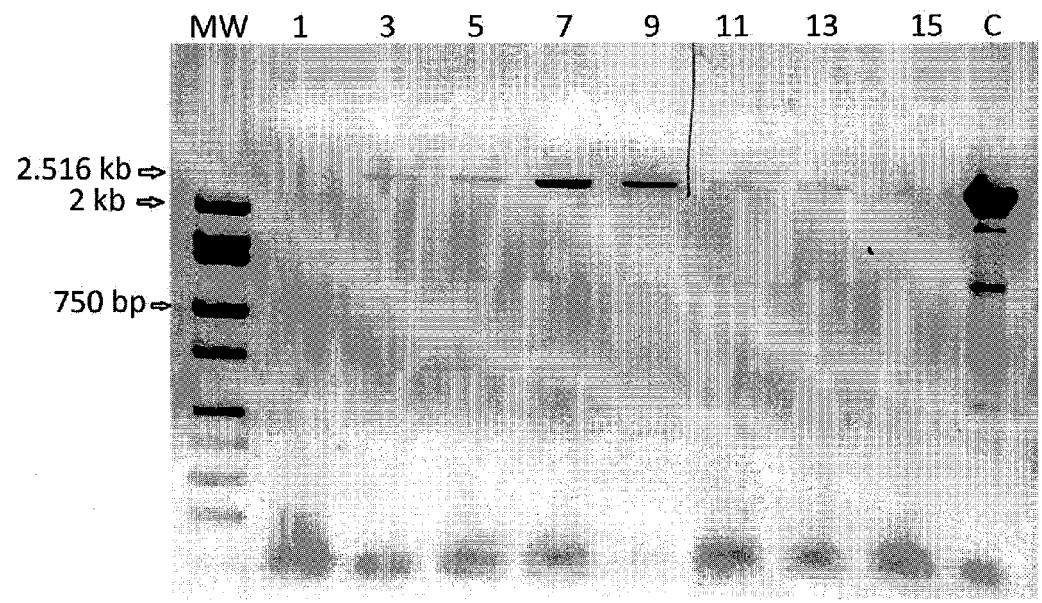

FIG. 1 illustrates an analysis of DNA extracted from 20 µL blood collected using a collection device with exemplary matrices and a collection device without any matrix—blood directly extracted without any matrix (blank control). For the exemplary matrices, DNA was extracted using two different DNA extraction reagents (OCC-1 or OCC-2) as detailed below. For the exemplary matrices, DNA was eluted in about 10 µL of 10 mM Tris-HCl pH 8.0, 0.1 mM EDTA pH 8.0 followed by incubation at 60° C. for 3-5 minutes. The tubes were centrifuged to collect the glass beads and the supernatant was aspirated. About 2 µL was used for PCR. Following PCR, about 10 µL aliquot of the PCR product was applied on a 2% agarose-ethidium bromide gel and electrophoretically resolved. Gel electrophoretic representation of the isolation of the genomic DNA FIG. 1A—Extracted DNA from the various matrices was used for genotyping Fragile X CGG repeat region using Gene Link™ GScan kit (Cat. #: 40-2004-15) (as described previously herein) and the PCR conditions were as provided in the product manual. Lane: 1=no matrix control; 2=Q-Tip cotton; 3=20% zein (OCC-1 buffer; Gene Link Catalog #; 40-4111-XX); 4=20% zein (OCC-2 buffer; Gene Link Catalog #; 40-4131-XX); 5=20% zein+20% glycerol (OCC-1 buffer); 6=20% zein+20% glycerol (OCC-2 buffer); 7=20% zein+10% gelatin (OCC-1 buffer); 8=20% zein+10% gelatin (OCC-2 buffer); C=male control DNA. FIG. 1B—DNA extracted from various matrices as stated in FIG. 1A and were used for amplification of a ~2.5 kb mitochondrial DNA (mtDNA) fragment. Lane: 1=no matrix control; 3=Q-Tip cotton; 5=20% zein; 7=20% zein & 20% glycerol; 9=20% zein & 10% gelatin; 13=20% zein; 15=20% zein & 20% glycerol; and C=male control DNA. All the samples extracted using the matrices amplified the 2.5 kb mtDNA fragment.

As shown in FIG. 1, the amplification of Fragile X specific gene fragments from the DNA extracted using exemplary matrices with composites of glycerol and gelatin showed DNA extraction using OCC-1 gave higher DNA yield as signified by the intensity of the PCR amplified fragments. This initial data also showed that the matrices used consistently yielded more amplified DNA as compared with cotton Q-Tip swab.

DNA Amplification—Short Tandem Repeat STR4Fa and STR3Fa Multiplex Amplification

STR4Fa and STR3Fa are multiplex PCR developed based on the FBI Combined DNA Index System (CODIS) STR loci and posted by the National Institute of Standards and Technology (NIST) at www.cstl.nist.gov/biotech/strbase/. Primer pairs, alleles, and amplification details are also available at the NIST website. Samples were processed for DNA extraction using Gene Link Omni-Mag DNA purification system (Catalog #: 40-4100-01) (as described previously herein). The final DNA elution was in 50 µL and 5 µL was used for the STR4Fa or STR3Fa amplification. The difference between STR4Fa and STR3Fa is the absence of X and Y fragment amplification primers in STRF3a. The final PCR primer concentration was 0.4 µM for all primers except the mtDNA primers were at 0.2 µM. All STR4Fa and STR3Fa PCR reaction volumes were 25 µL. The amplification thermal cycling was as follows; initial denaturation at 98° C. for 5 minutes and a hold at 62° C. while Taq polymerase was added to individual reaction tubes. After adding Taq polymerase the reaction was continued for 30 cycles as follows: denaturation at 94° C. for 30 seconds, annealing at 55° C. for 30 seconds and extension at 72° C. for 30 seconds. After 30 cycles there was one cycle at 72° C. for 7 minutes followed by hold at 12° C.

After amplification 10 µL aliquots were electrophoresed on a 2.2% agarose gel. The gel was stained with ethidium bromide and photographed. The amplification profile from touch and skin DNA samples are shown in FIG. 12. FIG. 12 shows the comparative results obtained from DNA extractions using all three kits.

Figure 12A:
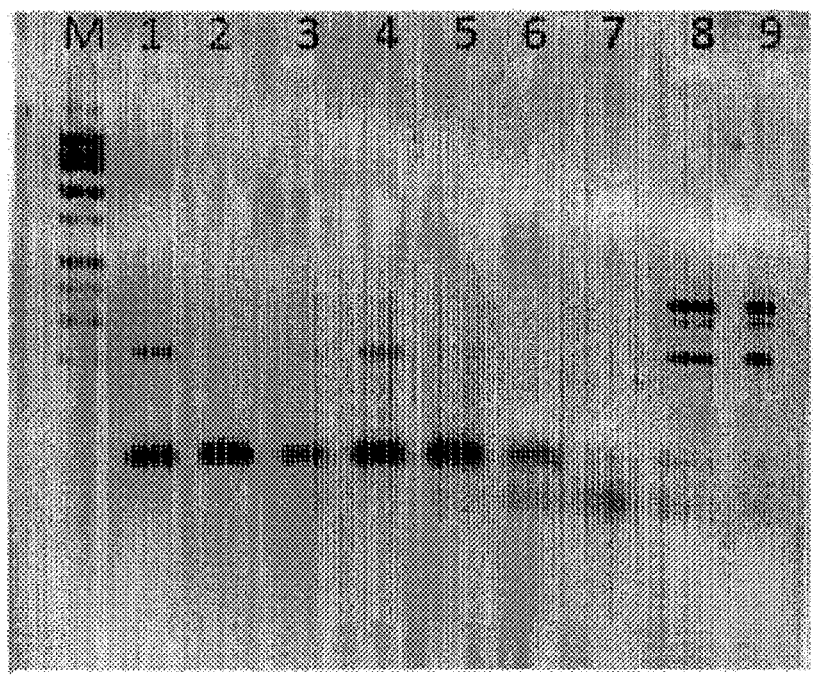
FIG. 12A and FIG. 12B show a gel electrophoretic representation of the isolation of extracted DNA according to some embodiments.
Figure 12B:
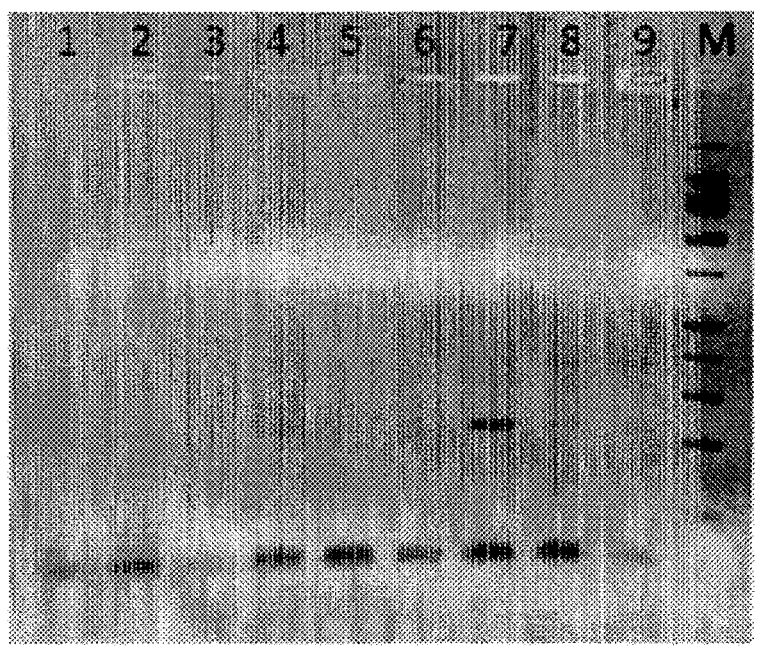

FIG. 12A and FIG. 12B illustrates the results of an exemplary collection procedure. All dilutions of blood shown in Table 4 were collected by Zein 20 matrix and processed for DNA extraction using three different kits: Gene Link Omni-Mag DNA purification system (OM) (Catalog #: 40-4100-01) (as described previously herein); ABI-ThermoFisher PrepFiler® (PF) (catalog#: 4463351) (as described previously herein); and Promega DNA-IQ System (PM) (Catalog #: DC-6701) (as described previously herein). Shown is a representative gel of short tandem repeat STR3Fa multiplex amplification and agarose gel electrophoresis results of DNA samples from Dilutions A, B, F & J as shown in Table 4. FIG. 12A—Lane 1-3 represents blood dilution A (2 µL); lanes 4-6 represent blood dilution B (0.2 µL); lane 7 represents a no template control (NTC); and lanes 8 and 9 represent control DNA samples. Lanes 1, 4, 7-9 samples were processed using Gene Link Omni-Mag DNA purification system (OM) (Catalog #: 40-4100-01) (as described previously herein); lanes 2 and 5 samples were processed with Promega DNA-IQ System (PM) (Catalog #: DC-6701) for DNA extraction (as described previously herein) and lanes 3 and 6 samples were processed with ABI-ThermoFisher PrepFiler® (PF) (catalog#: 4463351) for DNA extraction (as described previously herein). FIG. 12B—Lane 1-3 represents blood dilution F (2 µL of 1:100 diluted blood); lanes 4-6 represent blood dilution J (2 µL of 1:100 diluted blood); lane 7-9 represent blood dilution A (2 µL blood); and lanes represent 1, 4 and 7 samples processed using Gene Link Omni-Mag DNA purification system (OM) (Catalog #: 40-4100-01) (as described previously herein); lanes 2, 5 and 8 samples were processed with Promega DNA-IQ System (PM) (Catalog #: DC-6701) for DNA extraction (as described previously herein) and lanes 3, 6 and 9 samples were processed with ABI-ThermoFisher PrepFiler® (PF) (catalog#: 4463351) for DNA extraction (as described previously herein).

The zein matrix was able to lift DNA from touch DNA samples and from reverse touch DNA samples that yielded STR profile. The reverse touch DNA sampling capability to generate a DNA profile is an important application in DNA Biometrics. Consistently, Gene Link Omni-Mag DNA purification system (OM) (described previously herein) yielded more DNA as compared to other two extraction kits.

DNA Recovery

Figure 6:
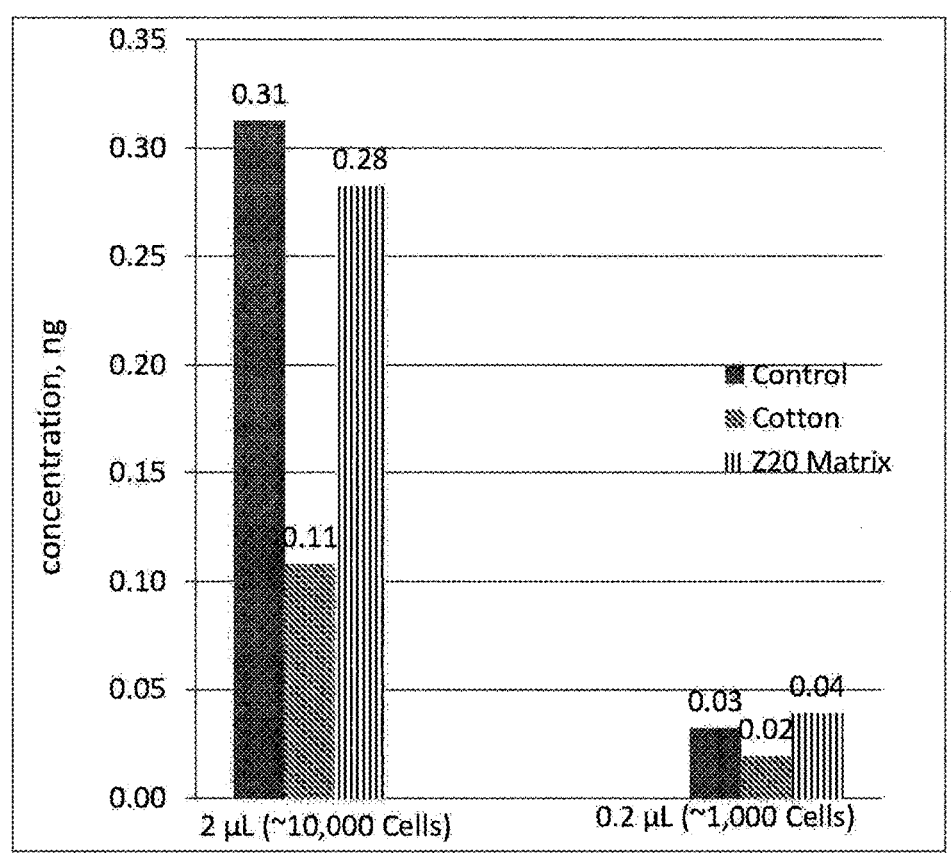
FIG. 6 shows a graphical illustration comparing DNA extraction from blood using various methods and collection matrices.
Figure 7:
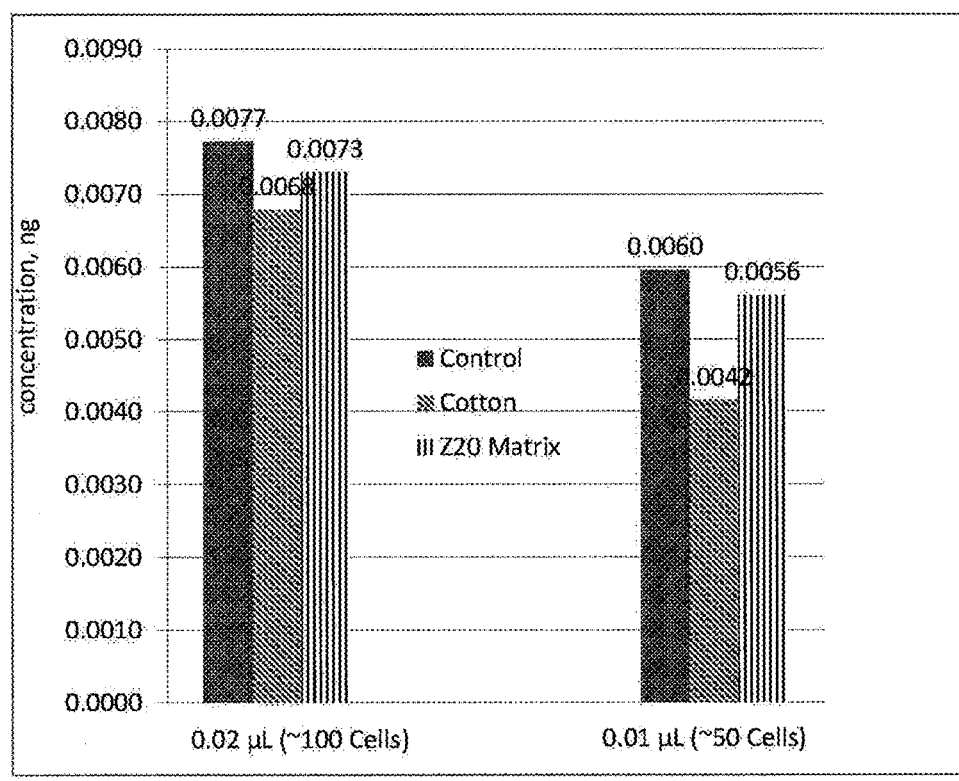
FIG. 7 shows a graphical illustration comparing DNA extraction from dilutions of blood using various methods and collection matrices.

FIG. 6 and FIG. 7 show the results of DNA recovery from various blood dilutions as a representative of cell counts and compared to DNA recovery using cotton swab, Z20 matrix, and control sample directly processed for DNA extractions using Gene Link Omni-Mag DNA purification system (OM) (Catalog #: 40-4100-01) (described previously herein) followed by DNA quantitation (using 2 µL) using Promega Plexor HY System (Catalog #: DC1001). Using the Promega Plexor® HY system, a serial dilution of a known concentration of human male genomic DNA was used to generate a concentration standard curve to plot and determine an unknown human DNA concentration using the Plexor® Analysis Software. Briefly, a reaction setup premix containing 10 µL of Plexor® HY 2X Master Mix, 7 µL of amplification grade water, 1 µL of Plexor® HY 20X Primer/IPC Mix, and 2 µL of the appropriate DNA standard or unknown DNA were added to the appropriate wells of a 96 well plate. The plate(s) contained samples of unknown concentration in duplicate or triplicate, standard DNA dilution reactions in duplicate (DNA standards contained the following concentration of DNA: 50 ng/µL, 10 ng/µL, 2 ng/µL, 0.4 ng/µL, 0.08 ng/µL, 0.016 ng/µL and 0.0032 ng/4), and a no template control (NTC) blank containing 2 µL Low TE (10 mM Tris-HCl pH 8.0, 0.1 mM EDTA pH 8.0). Thermal cycling was performed with the following conditions:

1 cycle of initial denaturation at 95° C. for 2 minutes;
38 cycles of:
denaturation at 95° C. for 5 seconds and
annealing and extension at 60° C. for 35 seconds.

After the thermal cycling was completed, all amplification, melt and dissociation data were exported for analysis by the Plexor® Analysis Software, which constructed a standard curve with the values of the known human genomic DNA dilution reactions and plotted the unknown samples to determine the DNA concentration.

FIG. 6 illustrates the results of an exemplary collection procedure in which 2 µL and 0.2 µL of blood were used as control and compared to blood collected using cotton swab and Z20 matrix as described in FIG. 2. The blood spots were processed for DNA extraction using Gene Link Omni-Mag DNA purification system (OM) (Catalog #: 40-4100-01) (described previously herein) followed by DNA quantitation (using 2 µL) using Promega Plexor HY System (Catalog #: DC1001). Shown are DNA quantification data for 2 µL and 0.2 µL blood samples collected using Z20 matrix. The DNA recovery for 2 µL blood for cotton swab was ~35% and from Z20 matrix was ~90%. For 0.2 µL the recovery from cotton swab was ~67% and from Z20 matrix was greater than 100%.

FIG. 7 illustrates the results of an exemplary collection procedure in which varying dilutions of blood were used as control and compared to blood collected using cotton swab and Z20 matrix as outlined in FIG. 2. The blood spots were processed for DNA extraction using Gene Link Omni-Mag DNA purification system (OM) (Catalog #: 40-4100-01) (as described previously herein) followed by DNA quantitation (using 2 µL) using Promega Plexor HY System (Catalog #: DC1001). Shown are quantification data for 0.02 µL (~100 cells) and 0.01 µL (~50 cells) blood. Trace quantity DNA recovery for 100 cells from cotton swab was ~88% as compared to ~95% from Z20 matrix, and DNA recovery from 50 cells from cotton swab was ~70% as compared to ~93% from Z20 matrix.

These results suggest superior performance of the matrix Z20 in almost quantitative recovery of DNA.

Figure 8:
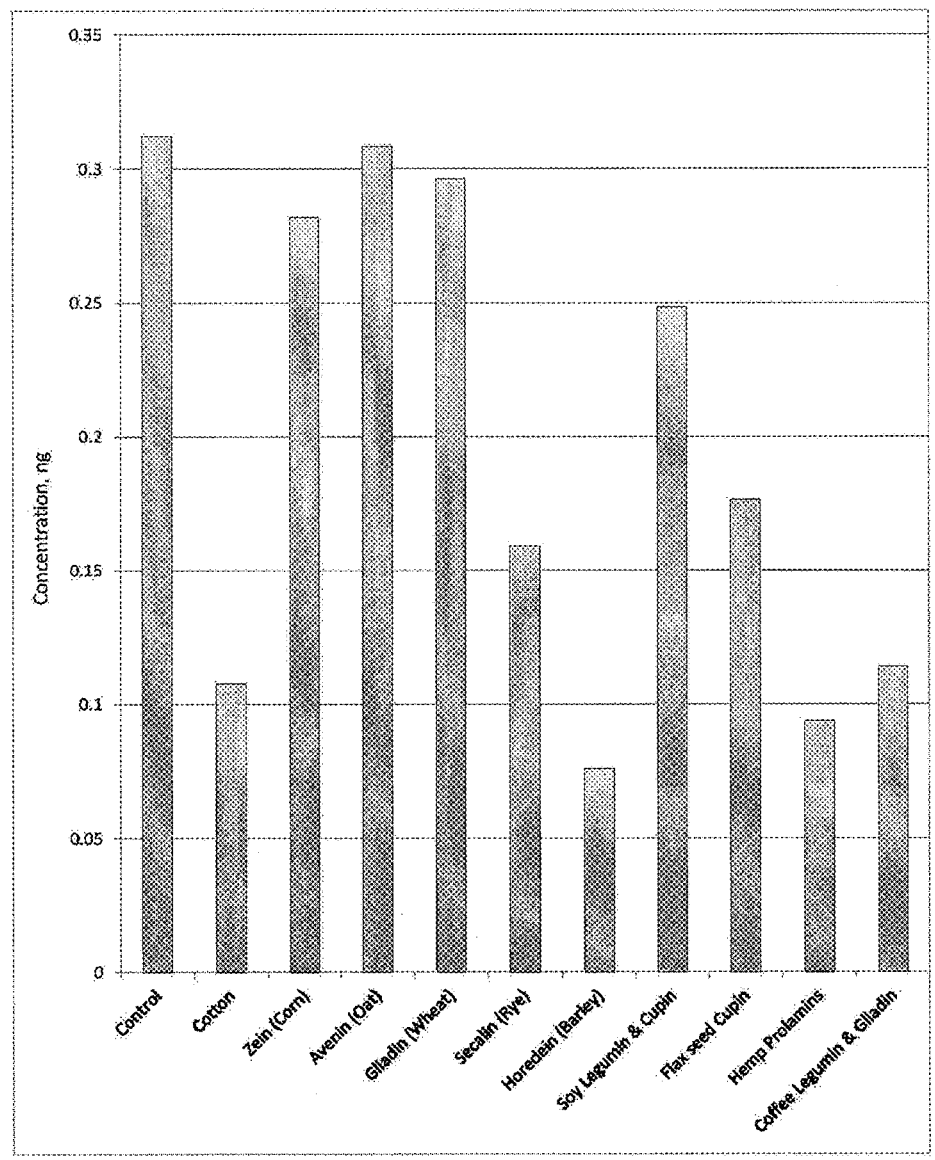
FIG. 8 shows a graphical illustration comparing extracted DNA quantification data collected by various methods and devices with different matrices.
Figure 9:
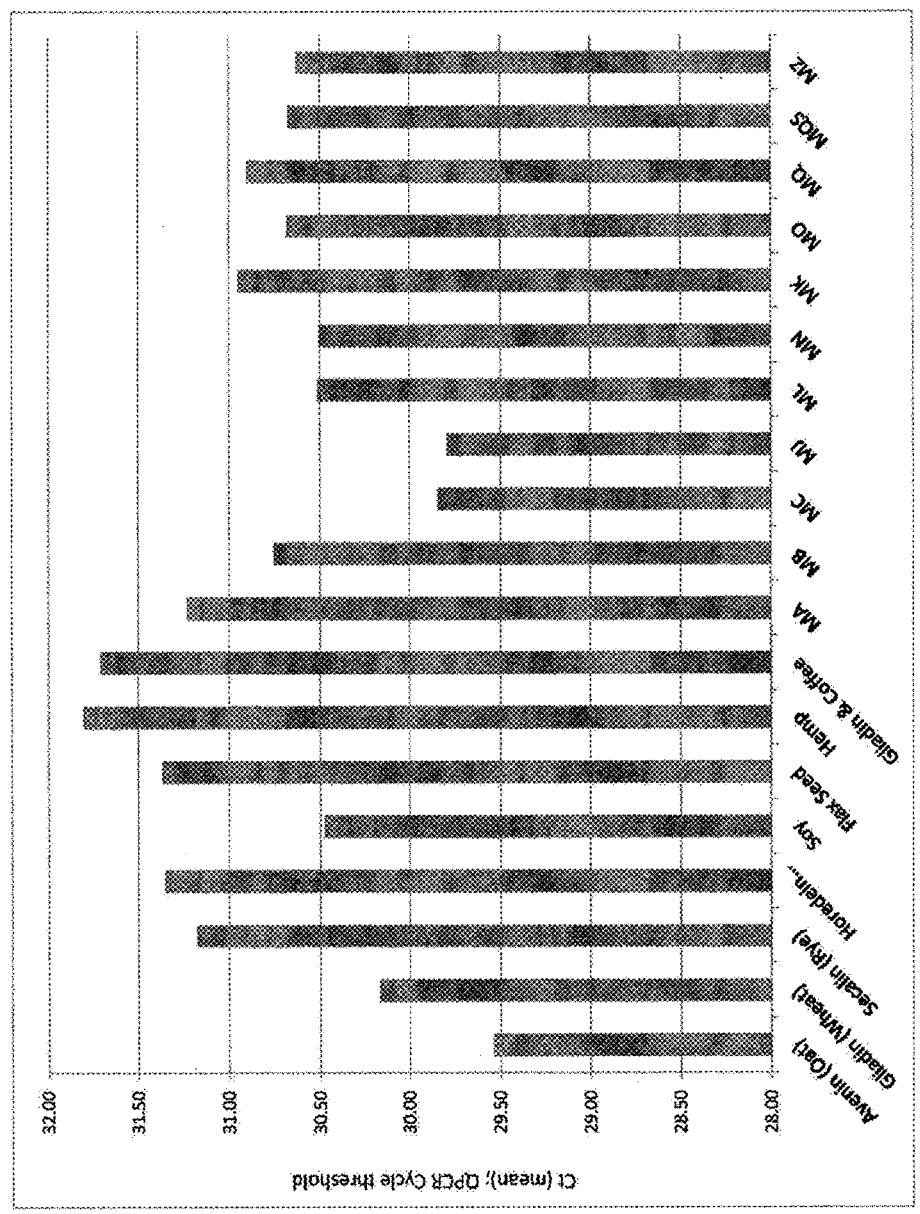
FIG. 9 shows a graphical illustration comparing extracted DNA quantification data collected using devices with various biopolymer matrices

FIG. 8 shows the results of DNA recovery from 2 µL blood using various prolamins as matrices. FIG. 8 illustrates the results of an exemplary collection procedure in which various prolamin and legume seed storage proteins were used as the biopolymer for preparing the matrix composite. A standard sample collection assay for 2 µL whole blood was used as described in FIG. 2. All samples were processed as detailed in the description of FIG. 6 and FIG. 7. The extracted DNA was quantified using Promega Plexor XY System (catalog# DC1001). All proteins and their composites performed well in sample collection and recovery. Shown are DNA quantification data for 2 µL whole blood using 2 µL DNA. Some proteins with lower recovery were improved by the addition of varying amounts of excipients and other chemicals (as shown in FIG. 9). Cotton swab DNA recovery was ~34% compared to ~90% from Zein and 97% from Avenin. The lowest recovery was from horedein (barley), with a recovery of 24%. These data suggest the viability of the use of prolamins as matrices.

FIG. 9 illustrates the results of an exemplary collection procedure in which the biopolymers and composites listed in Table 4 were used for the production of matrices. A standard collection assay for 2 µl of whole blood was used as described for FIG. 2. Briefly, 2 µL and 1 µL blood dilutions were applied on glass or plastic plates, allowed to dry and collected as shown in FIG. 2D. Samples were processed for DNA extraction using Gene Link Omni-Mag DNA purification system (Catalog #: 40-4100-01) (as described previously herein). The final DNA elution was in 50 µL and 5 µL was used for the STRF3a analysis. STRF3a is a 3 locus short tandem repeat amplification kit. After amplification, 10 µL aliquots were electrophoresed on a 2.2% agarose gel. The gel was stained with ethidium bromide and photographed. The extracted DNA was quantified using QPCR with a progesterone receptor (PGR) probe. Cycle threshold (Ct) values plotted for each matrix. Lower Ct values signify higher DNA concentration. The abbreviations listed on the X-axis are defined in Table 4. The results show the robust amplification profile from Z20 matrix as compared to cotton swab and control samples. The intensity of the fragments are comparable to those in the control. Avenin gave the lowest Ct value of 29.5, while hemp gave the highest Ct value greater than 31.50. All matrices performed well in comparison to zein. Some proteins with lower recovery were improved by the addition of varying amounts of excipients and other chemicals as discussed herein.

TABLE 4

Matrices used in FIG. 9.

| Abbreviation | Components |
| --- | --- |
| MA | Zein 20% & 20% glycerol |
| MB | Zein 20% & 10% PEG 7000-9000 |
| MC | Zein 20% & 10% polyvinyl alcohol |

TABLE 4-continued

Matrices used in FIG. 9.

| Abbreviation | Components |
| --- | --- |
| MJ | Zein 20% & 2% Sodium dodecyl sulfate |
| ML | Zein 20%, 10% glycerol & 1% sodium dodecyl sulfate |
| MN | Zein 20%, 20% glycerol & 2% sodium dodecyl sulfate |
| MK | Zein 20%, 10% glycerol & 2% sodium dodecyl sulfate |
| MO | Zein 20% & 10% glycerol |
| MQ | Zein 20%, 10% glycerol and 2% trehalose |
| MQS | Zein 20%, 10% glycerol, 2% trehalose and 2% SDS |
| MZ | Zein 20% |

Figure 10:
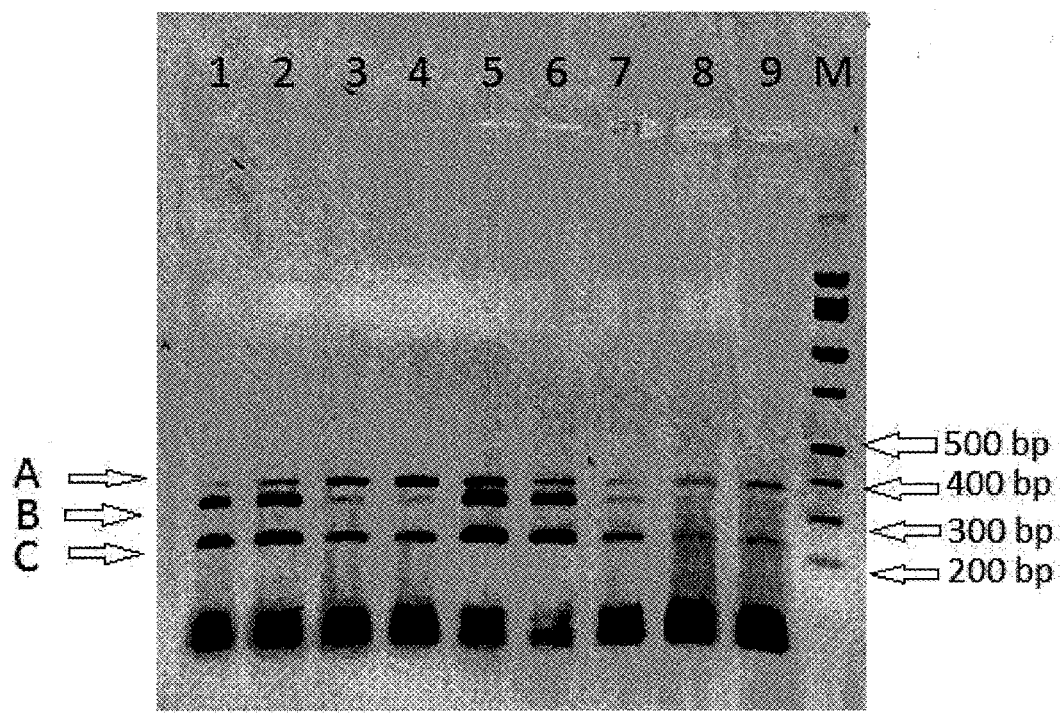
FIG. 10 and FIG. 11 show a gel electrophoretic representation of the isolation of extracted DNA according to some embodiments.

FIG. 10 illustrates the results of STR3Fa PCR amplification comparing DNA collection and extraction using direct control, cotton, and Z20 matrix. As a control, blood or appropriately diluted blood samples were applied directly in the tube and processed for DNA extraction. The representative gel picture shows short tandem repeat STR3Fa multiplex amplification and agarose gel electrophoresis results of DNA samples from 1 µL and 2 µL whole blood, control, collected by cotton swab or zein matrix. Lanes 1 & 2 represent 2 µL blood control; lanes 3 & 4 represent 2 µL blood collected using cotton swab; lanes 5 & 6 represent collection using Z20 matrix; lane 7 represents 1 µL blood control; lane 8 represents blood collected using cotton swab; and lane 9 represents blood collected using Z20 matrix. Lane M is a molecular weight marker. The amplified fragments A, B, and C represent a multiplex short tandem repeat (STR) PCR for fragment A of ~364 bp from mtDNA, fragment B of ~315 from CSF1PO gene and fragment C of ~223 bp for FES/FPS. The results show the amplification intensity being more in Z20 matrix collected samples versus the cotton swab. These preliminary single gene amplification as performed and shown in FIGS. 1A and 1B and with a multiplex amplification of 3 gene locus in FIG. 10 illustrate that there is higher recovery of DNA from samples collected by Z20 matrix as compared to cotton swab.

Figure 11:
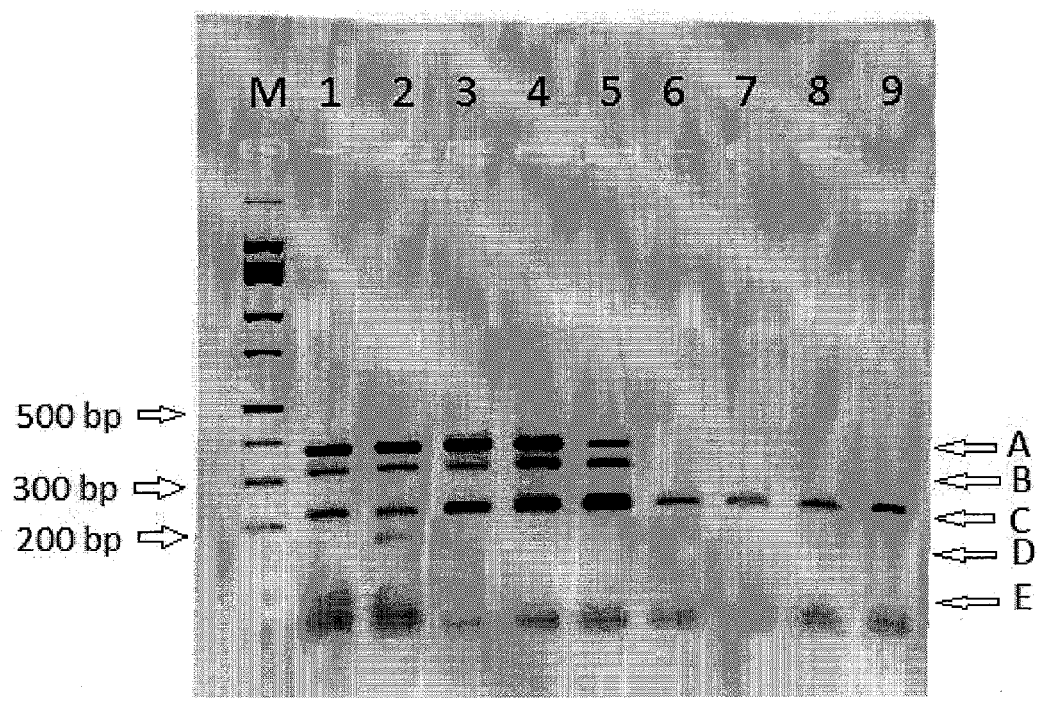

FIG. 11 illustrates the results of an exemplary collection procedure, showing short tandem repeat (STRF4a & STR3Fa) multiplex amplification and agarose gel electrophoresis results of Z20 matrix collected DNA samples from skin lift and touch DNA samples. Briefly, matrix Z20 was applied on the upper hand as shown in FIG. 5. The dried films were collected and processed for DNA extraction using Gene Link Omni-Mag DNA purification system (Catalog #: 40-4100-01) (as described previously herein). The final DNA elution was in 20 µL and 5 µL was used for the STR analysis. Lane M: molecular weight marker. Lane 1 and 2 represents STR4Fa 5 loci multiplex amplification from control female (lane 1) and from control male (lane 2) DNA samples; Lanes 3-9 represent 3 loci STR amplification as shown in FIG. 10. Lanes 3-5—control DNA samples; Lanes 6 & 7—subject 1 skin lift and touch DNA samples; Lanes 8 & 9—subject 2 skin lift and touch DNA samples. The amplified fragments A, B, and C represent a multiplex short tandem repeat (STR) PCR for fragment A of ~364 bp from mtDNA, fragment B of ~315 from CSF1PO gene, fragment C of ~223 bp for FES/FPS, fragment D of 167 bp from the Y chromosome, and fragment E of 76 bp from the X chromosome. The gel based STR analysis is less sensitive than the fluorescent based STR analysis typically used for forensic cases. Fluorescent STR analysis results are presented in Table 5.

Table 5 summarizes the results of the DNA profile obtained using ThermoFisher GlobalFiler® amplification kit from extracted DNA of samples listed in Table 4 of various blood dilutions, touch sampling, reverse sampling, and a three person fingerprint sample collection. GlobalFiler® PCR Amplification Kit (a 6-dye, 24-locus STR kit that is used extensively by forensic DNA labs worldwide) was used to generate the DNA profile. The amplified samples were run on the 3500 Genetic Analyzer, and the data was analyzed using GeneMapper® ID X Version 1.5 to generate a DNA profile. The results showed 100% and 97.7% allele recoveries at 1:100 and 1:200 blood dilutions that correspond to ~100 and 50 cells, respectively; the swab sample allele recoveries were 27.7 and 38.6 respectively. Similarly, the multiple fingerprint DNA samples of three persons gave a 98.8% allele recovery and 74% recovery for swab samples. The reverse touch sample with matrix K105 gave 100% allele recovery.

The results demonstrate the superior and almost quantitative yields of DNA recovery and DNA profile allele recovery using the disclosed biopolymer matrices. The triple fingerprint mixture of three individuals touch DNA allele recovery of 98.8% is demonstrated using biopolymer matrix K105.

TABLE 5

DNA Profile Amplification Results

| Sample Name | Matrix Type | Alleles in sample | Alleles recovered | Percentage recovery |
| --- | --- | --- | --- | --- |
| Sample/Blood Dilution | | | | |
| Dilution A. 2 µL blood | None Control | 44 | 44 | 100 |
| Dilution B. 2 µL of 1:10 blood | None Control | 44 | 44 | 100 |
| Dilution F. 2 µL of 1:100 blood | None Control | 44 | 39 | 88.6 |
| Dilution J. 2 µL of 1:200 blood | None Control | 44 | 44 | 100 |
| Dilution A. 2 µL blood | Purflock ® Swab | 44 | 44 | 100 |
| Dilution B. 2 µL of 1:10 blood | Purflock ® Swab | 44 | 44 | 100 |
| Dilution F. 2 µL of 1:100 blood | Purflock ® Swab | 44 | 12 | 27.7 |
| Dilution J. 2 µL of 1:200 blood | Purflock ® Swab | 44 | 17 | 38.6 |
| Dilution A. 2 µL blood | Omni-Matrix Z20 | 44 | 44 | 100 |

TABLE 5-continued

DNA Profile Amplification Results

| Sample Name | Matrix Type | Alleles in sample | Alleles recovered | Percentage recovery |
|---|---|---|---|---|
| Dilution B. 2 µL of 1:10 blood | Omni-Matrix Z20 | 44 | 44 | 100 |
| Dilution F. 2 µL of 1:100 blood | Omni-Matrix Z20 | 44 | 44 | 100 |
| Dilution J. 2 µL of 1:200 blood | Omni-Matrix Z20 | 44 | 43 | 97.7 |
| Fingerprint/Touch/Trace DNA | | | | |
| Individual 1 | *Purflock ® Swab | 40 | 4 | 10 |
| Individual 2 | *Purflock ® Swab | 41 | 16 | 39 |
| Individual 3 | *Purflock ® Swab | 43 | 20 | 46.5 |
| Triple- Individual 1, 2 & 3 | *Purflock ® Swab | 86 | 64 | 74 |
| Individual 1 | Omni-Matrix K105 | 40 | 9 | 22.5 |
| Individual 2 | Omni-Matrix K105 | 41 | 26 | 63.4 |
| Individual 3 | Omni-Matrix K105 | 43 | 10 | 23.2 |
| Triple- Individual 1, 2 & 3 | Omni-Matrix K105 | 86 | 85 | 98.8 |
| Reverse Touch | | | | |
| Individual 1 | Omni-Matrix K105 | 40 | 2 | 5 |
| Individual 2 | Omni-Matrix K105 | 41 | 41 | 100 |

*Purflock ® Swab manufactured by Puritan was used as one of the best swabs used for collecting trace DNA samples The biopolymer matrix Z20 and K105 were compared to PurFlock® Ultra Swab for their ability to collect small and trace diluted blood stains off of a non-porous surface by swabbing. A control was used in which diluted blood samples were directly extracted for DNA without swabbing. These tests were performed in triplicate.

In addition, two (2) sets of fingerprints from three different individuals were placed on a sterilized non-porous glass surface. Then a mixture was made by placing fingerprints from the three individuals on the same surface. This experiment was performed in triplicate. One set was processed for collection using K105 matrix, another set was swabbed using slightly dampened Puritan PurFlock® Ultra swabs.

All DNA extractions were performed using the PrepFiler® Express Chemistry on the Automate Express™ Robot from ThermoFisher using standard protocols for swab extractions. The samples were quantitated using Thermo Fisher Quantifiler Trio® Chemistry on the 7500 Real Time PCR Instrument. A representative set of the samples were then amplified using ThermoFisher GlobalFiler® PCR Amplification Kit and the 9700 Thermal Cycler to generate a 24 locus STR DNA amplification fragments. The amplified samples were run on the 3500 Genetic Analyzer, and the data was analyzed using GeneMapper® ID X Version 1.5 to generate a DNA profile. Table 5 summarizes the allele DNA profile obtained and expected in each sample, the alleles recovered, and the percentage recovery using different sample collection.

Summary

The results show the viability of the use of proteins and polysaccharides that are about 0% to about 10% dissolvable in water at a pH of about 6 to about 8 and at ambient temperature but about 10% to 100% dissolvable in a chaotropic solvent or an organic solvent for use as matrices. The matrices can be optimized with various composites of biopolymers and surfactants. The disclosed matrices allow for the release of the collected biological macromolecule, which will be available for subsequent analysis and testing.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

EMBODIMENTS

The following list of embodiments is intended to complement, rather than displace or supersede, the previous descriptions.

Embodiment 1

A matrix for isolating a biological macromolecule from a biological sample, the matrix comprising:

a biopolymer capable of binding to the biological macromolecule, wherein the biopolymer is about 0% to about 10% dissolvable in water at a pH of about 6 to about 8 and at ambient temperature but is about 10% to 100% dissolvable in a chaotropic solvent or an organic solvent, and wherein the biopolymer is not squid ring teeth protein; and a surfactant, excipient, or combination thereof.

Embodiment 2

The matrix of embodiment 1, wherein the biopolymer comprises zein and the surfactant comprises ethanol.

Embodiment 3

The matrix of embodiment 2, wherein the biopolymer comprises about 1% to about 50% zein.

Embodiment 4

The matrix of any one of the previous embodiments, further comprising a carbohydrate, salt, organic compound, inorganic compound, or a combination thereof.

Embodiment 5

The matrix of embodiment 4, wherein the salt is sodium chloride, ammonium sulfate, ammonium chloride, or a combination thereof.

Embodiment 6

The matrix of any one of the previous embodiments, wherein the matrix is configured as a composite matrix, layered matrix, extruded fiber, adhesive film, adhesive pad, adhesive spray, foam, liquid, or powder.

Embodiment 7

The matrix of any one of the previous embodiments, further comprising an applicator, wherein the applicator serves as a substrate for the biopolymer.

Embodiment 8

The matrix of embodiment 7, wherein the applicator is a swab, a pestle, a tape, a spin column, a pad, a fabric, a filter, a membrane, or any material configured for wiping a surface.

Embodiment 9

The matrix of any one of the previous embodiments, wherein the biological macromolecule is DNA, RNA, protein, carbohydrate, lipid, small molecule, cellular organic or inorganic component, or a combination thereof.

Embodiment 10

A device for isolating a biological macromolecule from a biological sample, the device comprising:
 a matrix comprising
  a biopolymer capable of binding to the biological macromolecule, wherein the biopolymer is about 0% to about 10% dissolvable in water at a pH of about 6 to about 8 and at ambient temperature but is about 10% to 100% dissolvable in a chaotropic solvent or an organic solvent, and wherein the biopolymer is not squid ring teeth protein; and
 a surfactant, excipient, or combination thereof; and
 an applicator, wherein the applicator serves as a substrate for the matrix.

Embodiment 11

The device of embodiment 10, wherein the biopolymer comprises zein and the surfactant comprises ethanol.

Embodiment 12

The device of embodiment 11, wherein the biopolymer comprises about 1% to about 50% zein.

Embodiment 13

The device of any one of embodiments 10-12, further comprising a carbohydrate, salt, organic compound, inorganic compound, or a combination thereof.

Embodiment 14

The device of embodiment 13, wherein the salt is sodium chloride, ammonium sulfate, ammonium chloride, or a combination thereof.

Embodiment 15

The device of any one of embodiments 10-14, wherein the matrix is configured as a composite matrix, layered matrix, extruded fiber, adhesive film, adhesive pad, adhesive spray, foam, liquid, or powder.

Embodiment 16

The device of any one of embodiments 10-15, wherein the applicator is a swab, a pestle, a tape, a spin column, a pad, a fabric, a filter, a membrane, or any material configured for wiping a surface.

Embodiment 17

The device of any one of embodiments 10-16, wherein the biological macromolecule is DNA, RNA, protein, carbohydrate, lipid, small molecule, cellular organic or inorganic component, or a combination thereof.

Embodiment 18

A method of isolating a biological macromolecule from a biological sample, comprising:
 contacting the biological sample with the matrix of any one of embodiments 1-9 or the device of any one of embodiments 10-17;
 incubating the matrix or device in a chaotropic solvent or an organic solvent; and
 isolating the biological macromolecule.

Embodiment 19

The method of embodiment 18, wherein the biological macromolecule is DNA, RNA, protein, carbohydrate, lipid, small molecule, cellular organic or inorganic component, or a combination thereof.

Embodiment 20

The method of embodiment 18 or 19, further comprising processing the biological macromolecule for genetic fragment analysis, single nucleotide polymorphism (SNP) analysis, Quantitative PCR (real time PCR), DNA or RNA amplification analysis, DNA or RNA cloning and library preparation, small molecule (drug) analysis, protein analysis, lipid analysis, carbohydrate analysis, organic analysis, inorganic analysis, or any combination thereof.

Embodiment 21

The method of any one of embodiments 18-20, wherein the method further comprises collecting the matrix prior to the incubating step.

Embodiment 22

A method of analyzing a test sample for the presence of a biological macromolecule, comprising:
contacting the test sample with the matrix of any one of embodiments 1-9 or the device of any one of embodiments 10-17;
incubating the matrix or device in a chaotropic solvent or an organic solvent; and
analyzing the solvent for the presence of the biological macromolecule.

Embodiment 23

The method of embodiment 22, wherein the biological macromolecule is DNA, RNA, protein, carbohydrate, lipid, small molecule, cellular organic or inorganic component, or a combination thereof.

Embodiment 24

The method of embodiment 22 or 23, wherein the analyzing is genetic fragment analysis, DNA or RNA amplification analysis, DNA or RNA cloning and library preparation, small molecule (drug) analysis, protein analysis, lipid analysis, carbohydrate analysis, organic analysis, inorganic analysis, or any combination thereof.

Embodiment 25

The method of any one of embodiments 22-24, wherein the method further comprises collecting the matrix prior to the incubating step.

Embodiment 26

A device for collecting, storing, transporting, and/or processing a biological sample, the device comprising a tube and a spatula, wherein the tube and the spatula are reversibly connected.

Embodiment 27

The device of embodiment 26, wherein the tube and the spatula are reversibly connected via a snap break ring, a slide-in ring, or a screw-in ring.

What is claimed:
1. A matrix for isolating a biological macromolecule from a biological sample, the matrix comprising:
Zein in a final concentration of 70% to 85% aqueous ethanol;
an excipient comprising Sodium Dodecyl Sulfate, N-Dodecyl-N,N-dimethyl-3-ammonio-1-propanesulfonate, 3-(N,N-dimethyl myristyl ammonio) propanesulfonate, polyoxyethylene (20) cetyl ether, polyethylene glycol (PEG) 7000-9000, or a combination thereof; and
a carbohydrate, salt, organic compound, inorganic compound, or a combination thereof.

2. The matrix of claim 1, wherein the excipient is Sodium Dodecyl Sulfate.

3. The matrix of claim 1, wherein the matrix comprises about 1% to about 50% zein.

4. The matrix of claim 1, wherein the salt is sodium chloride, ammonium sulfate, ammonium chloride, or a combination thereof.

5. The matrix of claim 1, further comprising an applicator, wherein the applicator serves as a substrate for the matrix, wherein the applicator is a swab, a pestle, a tape, a spin column, a pad, a fabric, a filter, a membrane, or any material configured for wiping a surface.

6. The matrix of claim 1, wherein the biological macromolecule is DNA, RNA, protein, carbohydrate, lipid, small molecule, cellular organic or inorganic component, or a combination thereof.

7. A device for isolating a biological macromolecule from a biological sample, the device comprising:
a matrix comprising:
zein in a final concentration of 70% to 85% aqueous ethanol; and
an excipient comprising Sodium Dodecyl Sulfate, N-Dodecyl-N,N-dimethyl-3-ammonio-1-propanesulfonate, 3-(N,N-dimethyl myristyl ammonio) propanesulfonate, polyoxyethylene (20) cetyl ether, polyethylene glycol (PEG) 7000-9000, or a combination thereof;
and an applicator, wherein the applicator serves as a substrate for the matrix.

8. The device of claim 7, wherein the excipient is Sodium Dodecyl Sulfate.

9. The device of claim 7, wherein the matrix comprises about 1% to about 50% zein.

10. The device of claim 7, further comprising a carbohydrate, salt, organic compound, inorganic compound, or a combination thereof.

11. The device of claim 10, wherein the salt is sodium chloride, ammonium sulfate, ammonium chloride, or a combination thereof.

12. The device of claim 7, wherein the applicator is a swab, a pestle, a tape, a spin column, a pad, a fabric, a filter, a membrane, or any material configured for wiping a surface.

13. The device of claim 7, wherein the biological macromolecule is DNA, RNA, protein, carbohydrate, lipid, small molecule, cellular organic or inorganic component, or a combination thereof.

14. A method of isolating a biological macromolecule from a biological sample, the method comprising:
contacting the biological sample with the matrix of claim 1;
incubating the matrix in a chaotropic solvent or an organic solvent; and
isolating the biological macromolecule.

15. The method of claim 14, wherein the biological macromolecule is DNA, RNA, protein, carbohydrate, lipid, small molecule, cellular organic or inorganic component, or a combination thereof.

16. The method of claim 14, further comprising processing the biological macromolecule for genetic fragment analysis, single nucleotide polymorphism analysis, Quantitative PCR, DNA or RNA amplification analysis, DNA or RNA cloning and library preparation, small molecule analysis, protein analysis, lipid analysis, carbohydrate analysis, organic analysis, inorganic analysis, or any combination thereof.

17. The method of claim 14, wherein the method further comprises collecting the matrix prior to the incubating step.

18. A method of analyzing a test sample for the presence of a biological macromolecule, comprising:
   contacting the test sample with the matrix of claim 1;
   incubating the matrix in a chaotropic solvent or an organic solvent; and
   analyzing the solvent for the presence of the biological macromolecule.

19. The method of claim 18, wherein the biological macromolecule is DNA, RNA, protein, carbohydrate, lipid, small molecule, cellular organic or inorganic component, or a combination thereof.

20. The method of claim 18, wherein the analyzing is genetic fragment analysis, DNA or RNA amplification analysis, DNA or RNA cloning and library preparation, small molecule analysis, protein analysis, lipid analysis, carbohydrate analysis, organic analysis, inorganic analysis, or any combination thereof.

21. The method of claim 18, wherein the method further comprises collecting the matrix prior to the incubating step.

* * * * *